(12) United States Patent
Cremonesi et al.

(10) Patent No.: US 10,577,361 B2
(45) Date of Patent: Mar. 3, 2020

(54) DOPAMINE D3 RECEPTOR ANTAGONISTS HAVING A MORPHOLINE MOIETY

(71) Applicant: Indivior UK Limited, Berkshire (GB)

(72) Inventors: Susana Cremonesi, Verona (IT);
Fabrizio Micheli, Verona (IT); Teresa Semeraro, Verano (IT); Luca Tarsi, Verona (IT)

(73) Assignee: INDIVIOR UK LIMITED, Hull (GB)

( * ) Notice: Subject to any disclaimer, the term of this patent is extended or adjusted under 35 U.S.C. 154(b) by 0 days.

(21) Appl. No.: 15/767,328

(22) PCT Filed: Oct. 13, 2016

(86) PCT No.: PCT/GB2016/053169
§ 371 (c)(1),
(2) Date: Apr. 10, 2018

(87) PCT Pub. No.: WO2017/064488
PCT Pub. Date: Apr. 20, 2017

(65) Prior Publication Data
US 2018/0297990 A1    Oct. 18, 2018

(30) Foreign Application Priority Data
Oct. 13, 2015 (GB) .................. 1518124.1

(51) Int. Cl.
*C07D 413/12* (2006.01)
*C07D 413/14* (2006.01)
*C07D 417/14* (2006.01)

(52) U.S. Cl.
CPC ......... *C07D 413/12* (2013.01); *C07D 413/14* (2013.01); *C07D 417/14* (2013.01); *C07B 2200/07* (2013.01)

(58) Field of Classification Search
CPC ... C07D 413/12; C07D 413/14; C07D 417/14
See application file for complete search history.

(56) References Cited

FOREIGN PATENT DOCUMENTS

| | | |
|---|---|---|
| DE | 1 058 060 B | 5/1959 |
| EP | 0 307 121 A1 | 3/1989 |
| EP | 0 307 121 B1 | 3/1989 |
| FR | 2094499 A5 | 2/1972 |
| JP | 60-61569 A | 4/1985 |
| JP | 07-2848 A | 1/1995 |
| WO | WO-2004/052372 A1 | 6/2004 |
| WO | WO-2005/115985 A1 | 12/2005 |
| WO | WO-2008/026046 A1 | 3/2008 |

OTHER PUBLICATIONS

Kitano et al. Chem. Pharm. Bull. 40(3) 768-769 (1992).*
Registry No. 1294287-12-9, File Registry on STN, May 13, 2011.*
Burris, K.D. et al. (Feb. 1994). "Characterization of [$^{125}$I](R)-trans-7-hydroxy-2-[N-propyl-N-(3'-iodo-2'-propenyl)amino]tetralin binding to dopamine D3 receptors in rat olfactory tubercle," *J Pharmacol Exp Ther* 268(2):935-942.
Database Registry 1294287-12-9, entered STN May 13, 2011, 1 page.
Database Registry 1299160-59-0, entered STN May 24, 2011, 1 page.
Database Registry 1318886-93-9, entered STN Aug. 17, 2011, 1 page.
Database Registry 1322054-46-5, entered STN Aug. 23, 2011, 1 page.
Database Registry 1322418-68-7, entered STN Aug. 24, 2011, 1 page.
Database Registry 1625067-66-4, entered STN Sep. 24, 2014, 1 page.
Database Registry 1626889-45-9, entered STN Sep. 26, 2014, 1 page.
Database Registry 1385916-14-2, entered STN Aug. 3, 2012, 1 page.
Database Registry 1385612-68-9, entered STN Aug. 2, 2012, 1 page.
Database Registry 1302364-04-0, entered STN May 29, 2011, 1 page.
Database Registry 1298648-80-2, entered STN May 22, 2011, 1 page.
Database Registry 1300878-80-1, entered STN May 26, 2011, 1 page.

(Continued)

*Primary Examiner* — Rebecca L Anderson
(74) *Attorney, Agent, or Firm* — Edward D. Grieff; Mintz, Levin, Cohn, Ferris, Glovsky and Popeo, P.C.

(57) ABSTRACT

The disclosure provides compounds of formula (I) or pharmaceutically acceptable salts thereof: The disclosure also provides processes for their preparation, intermediates used in these processes, pharmaceutical compositions containing them, and their use as modulators of dopamine $D_3$ receptors, such as treating substance abuse or psychiatric diseases.

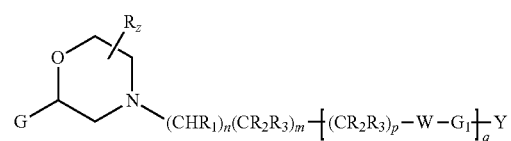

(I)

18 Claims, No Drawings

(56) References Cited

OTHER PUBLICATIONS

Database Registry 1301211-42-6, entered STN May 26, 2011, 1 page.
Database Registry 1387039-87-3, entered STN Aug. 6, 2012, 1 page.
Database Registry 1385772-68-8, entered STN Aug. 2, 2012, 1 page.
Database Registry 1626859-51-5, entered STN Sep. 26, 2014, 1 page.
Database Registry 1624799-41-2, entered STN Sep. 23, 2014, 1 page.
Database Registry 1389080-57-2, entered STN Aug. 12, 2012, 1 page.
Database Registry 1389002-69-0, entered STN Aug. 2, 2012, 1 page.
Durcan, M.J .et al. (1995). "Is clozapine selective for the dopamine $D_4$ receptor?" *Life Sci* 57(18):PL275-283.
Fleisher, D. et al. (May 1996). "Improved oral drug delivery: solubility limitations overcome by the use of prodrugs," *Advanced Drug Delivery Reviews* 199(2):115-130.

Levant B. et al. (Sep. 1997). "The $D_3$ dopamine receptor: neurobiology and potential clinical relevance," *Pharmacol Rev* 49(3):231-252.
MacKenzie, R.G. et al. (Jan. 1, 1994). "Characterization of the human dopamine $D_3$ receptor expressed in transfected cell lines," *Eur J Pharmacol* 266(1):79-85.
Micheli, F. et al. (Feb. 15, 2016, e-published Jan. 5, 2016). "Novel morpholine scaffolds as selective dopamine (DA) D3 receptor antagonists," *Bioorg Med Chem Lett* 26(4):1329-1332.
Pauwels, P.J. et al. (Sep. 2001). "Real-time analysis of dopamine: antagonist interactions at recombinant human $D^{2long}$ receptor upon modulation of its activation state," *Br J Pharmacol* 134(1):88-97.
Schwartz, J.C. et al. (Aug. 1993). "Dopamine $D_3$ receptor: basic and clinical aspects," *Clin Neuropharmacol* 16(4):295-314.
Schwartz, J.C. et al. (May 1998). "Functional implications of multiple dopamine receptor subtypes: the $D_1/D_3$ receptor coexistence," *Brain Research Reviews* 26:2-3:236-242.
Sokoloff, P. et al. (Sep. 13, 1990). "Molecular cloning and characterization of a novel dopamine receptor ($D_3$) as a target for neuroleptics," *Nature* 347(6289):146-151.
International Search Report dated Feb. 3, 2017, for PCT Application No. PCT/GB2016/053169, filed Oct. 13, 2016, 9 pages.
Written Opinion dated Feb. 3, 2017, for PCT Application No. PCT/GB2016/053169, filed Oct. 13, 2016, 12 pages.

* cited by examiner

DOPAMINE D3 RECEPTOR ANTAGONISTS HAVING A MORPHOLINE MOIETY

CROSS-REFERENCE TO RELATED APPLICATIONS

This application is a Section 371 US National Phase of PCT/GB2016/053169 filed Oct. 13, 2016, which claims priority to United Kingdom Application No. GB1518124.1 filed Oct. 13, 2015, the disclosures of which are incorporated by reference herein in their entirety.

BACKGROUND

Dopamine receptors are prominent in regulating several aspects of basic brain function. In particular, they are necessary for the normal tasks of the regions they innervate, including motor behavior, motivation, and working memory. Dopamine receptors are also a central element in the brain reward system that controls the learning of many behaviors. There are two main classes of dopamine receptors, D1 and D2, which respectively stimulate and inhibit adenylyl cyclase. Further research revealed the existence of two D1-like receptors, D1 and D5, and three D2-like receptors, D2, D3, and D4.

The selective distribution of the dopamine D3 receptors onto key neurocircuits that underlie the processing of motivationally relevant events has made this target a main focus of significant drug discovery efforts over the last decade. However, identifying selective pharmacological agents for D3 receptors is an ongoing challenge.

Disclosed herein, inter alia, are solutions to these and other problems in the art.

SUMMARY

A new class of compounds which have affinity for dopamine receptors, in particular the dopamine $D_3$ receptor, is described herein. These compounds are useful in treating conditions where modulation, especially antagonism or inhibition, of the dopamine $D_3$ receptor is beneficial The disclosure provides compounds of Formula (I) and pharmaceutically acceptable salts thereof:

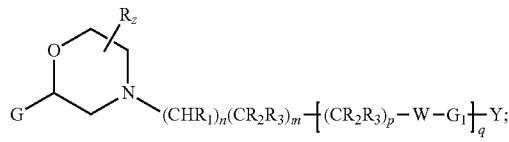
(I)

wherein the substituents are defined herein.

The compound of Formula (I) can be a compound of Formula (IA) or a pharmaceutically acceptable salt thereof:

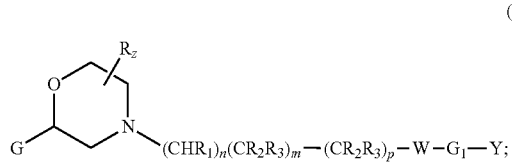
(IA)

wherein the substituents are defined herein.

The disclosure provides methods of treating dopamine D3 receptor diseases by administering therapeutically effective amounts of the compounds described herein to patients in need. A dopamine D3 receptor disease is any disease which can be treated through modulation, preferably antagonization, of the dopamine D3 receptor. Such dopamine D3 receptor diseases include psychiatric diseases, such as psychosis, psychotic diseases, and schizophrenia. Other dopamine D3 receptor diseases include addictions or dependencies, such as substance dependency, including alcohol dependency, opioid dependency, and the like.

These and other aspects of the disclosure are described in more detail herein.

DETAILED DESCRIPTION

The present invention provides a compound of formula (I) or a pharmaceutical acceptable salt thereof:

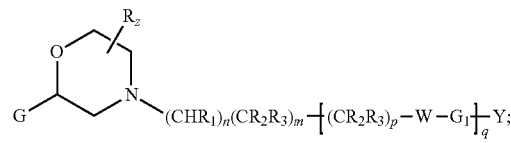
(I)

wherein

G is aryl or a 5-6 membered heteroaromatic group or 8-11 membered heteroaromatic group, which may be benzofused or optionally substituted by 1, 2, 3 or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $C(=O)OR_4$, and combinations of two or more thereof;

W is S, $SO_2$, O, $CHR_2$, or $NR_4$;

n is 0 or 1;

m is 1 or 2;

p is 0, 1, or 2;

q is 0 or 1;

z is an integer from 1 to 7;

R is independently hydrogen or $C_{1-4}$alkyl;

$R_1$ is hydrogen, $C_{1-4}$alkyl, or $C_{1-4}$alkoxy;

$R_2$ and $R_3$ are each independently hydrogen, F, $C_{1-4}$alkyl, OH, or $C_{1-4}$alkoxy;

$R_4$ is hydrogen or $C_{1-4}$alkyl;

$G_1$ is a phenyl group or a 5-6-membered heteroaromatic group or a 8-11 membered heteroaromatic group, any of which groups may be optionally substituted by 1, 2, 3 or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_4$, and combinations of two or more thereof;

Y is H or phenyl, or a moiety selected from the group consisting of: 5-6 membered heteroaromatic group, saturated mono 3-7 membered carbocyclic group or 8-11 membered bicyclic carbocyclic group in which one or more atom carbons may be replaced by $NR_4$, O, S; any of which groups may be optionally substituted by one or two substituents selected from: halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $SO_2NH_2$, $C(=O)O_xR_4$ wherein x is 0 or 1, or Y'; and Y' is phenyl, or a 5-6-membered heteroaromatic group optionally substituted by 1 or 2 $R_2$ groups, with the proviso that $G_1$, Y and Y' are not simultaneously phenyl.

In embodiments of Formula (I), p is 1 or 2.
In embodiments of Formula (I), q is 0 and n is 0.
In embodiments of Formula (I), q is 1 and p is 0.
The present invention provides a compound of Formula (IA) or a pharmaceutical acceptable salt thereof:

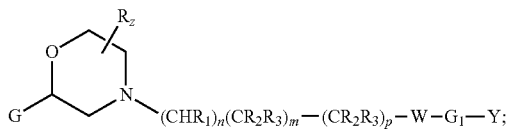
(IA)

wherein
G is aryl or a 5-6 membered heteroaromatic group, either of which can optionally be substituted by 1, 2, 3 or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $C(=O)OR_4$, and combinations of two or more thereof;
W is S, $SO_2$, O, $CHR_2$, or $NR_4$;
n is 0 or 1;
m is 1 or 2;
p is 1 or 2;
z is an integer from 1 to 7;
R is independently hydrogen or $C_{1-4}$alkyl;
$R_1$ is hydrogen, $C_{1-4}$alkyl, or $C_{1-4}$alkoxy;
$R_2$ and $R_3$ are each independently hydrogen, F, $C_{1-4}$alkyl, OH, or $C_{1-4}$alkoxy;
$R_4$ is hydrogen or $C_{1-4}$alkyl;
$G_1$ is a phenyl group or a 5-6-membered heteroaromatic group, either of which can optionally be substituted by 1, 2, 3 or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_4$, and combinations of two or more thereof;
Y is a moiety selected from the group consisting of: phenyl, a 5-6 membered heteroaromatic group, an saturated mono 3-7 membered carbocyclic group; any of which groups may be optionally substituted by one or two substituents selected from: halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $SO_2NH_2$, $C(=O)O_xR_4$ wherein x is 0 or 1, or Y'; and
Y' is phenyl or a 5-6-membered heteroaromatic group optionally substituted by 1 or 2 $R_2$ groups, with the proviso that $G_1$, Y and Y' are not simultaneously phenyl.

In embodiments, the substituents for the compound of Formula (IA) are as follows: G is aryl which can optionally be substituted by 1, 2, 3 or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $C(=O)OR_4$, and combinations of two or more thereof; W is S; n is 0 or 1; m is 1 or 2; p is 1 or 2; z is an integer from 1 to 7; R is independently hydrogen or $C_{1-4}$alkyl; $R_1$ is hydrogen, $C_{1-4}$alkyl, or $C_{1-4}$alkoxy; $R_2$ and $R_3$ are each independently hydrogen, F, $C_{1-4}$alkyl, OH, or $C_{1-4}$alkoxy; $R_4$ is hydrogen or $C_{1-4}$alkyl; $G_1$ is a 5-6-membered heteroaromatic group, which can optionally be substituted by 1, 2, 3 or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_4$, and combinations of two or more thereof; Y is a moiety selected from the group consisting of phenyl and a 5-6 membered heteroaromatic group, either of which can be optionally substituted by one or two substituents selected from: halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $SO_2NH_2$, $C(=O)O_xR_4$ wherein x is 0 or 1, or a combination of two or more thereof.

In embodiments, the substituents for the compound of Formula (IA) are as follows: G is aryl which can optionally be substituted by 1 or 2 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $C(=O)OR_4$, and combinations thereof; W is S; n is 0 or 1; m is 1 or 2; p is 1 or 2; z is an integer from 1 to 7; R is independently hydrogen or $C_{1-4}$alkyl; $R_1$ is hydrogen, $C_{1-4}$alkyl, or $C_{1-4}$alkoxy; $R_2$ and $R_3$ are each independently hydrogen, F, $C_{1-4}$alkyl, OH, or $C_{1-4}$alkoxy; $R_4$ is hydrogen or $C_{1-4}$alkyl; $G_1$ is a 5-membered heteroaromatic group, which can optionally be substituted by 1, 2, 3 or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_4$, and combinations of two or more thereof; Y is a moiety selected from the group consisting of phenyl and a 5- or 6-membered heteroaromatic group, any of which can optionally be substituted by one or two substituents selected from: halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $SO_2NH_2$, $C(=O)O_xR_4$ wherein x is 0 or 1, or a combination of two or more thereof.

In embodiments, the substituents for the compound of Formula (IA) are as follows: G is aryl which can optionally be substituted by 1 or 2 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $C(=O)OR_4$, and combinations thereof; W is S; n is 0 or 1; m is 1 or 2; p is 1 or 2; z is an integer from 1 to 7; R is independently hydrogen or $C_{1-4}$alkyl; $R_1$ is hydrogen, $C_{1-4}$alkyl, or $C_{1-4}$alkoxy; $R_2$ and $R_3$ are each independently hydrogen, F, $C_{1-4}$alkyl, OH, or $C_{1-4}$alkoxy; $R_4$ is hydrogen or $C_{1-4}$alkyl; $G_1$ is a 5-membered heteroaromatic group, which can optionally be substituted by 1, 2, 3 or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_4$, and combinations of two or more thereof; Y is a moiety selected from the group consisting of phenyl and a 5- or 6-membered heteroaromatic group, either of which can optionally be substituted by Y'; and Y' is phenyl or a 5-6-membered heteroaromatic group optionally substituted by 1 or 2 $R_2$ groups, with the proviso that $G_1$, Y and Y' are not simultaneously phenyl.

In embodiments, the substituents for the compound of Formula (IA) are as follows: G is aryl which can optionally be substituted by 1 or 2 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $C(=O)OR_4$, and combinations thereof; W is S; n is 1; m is 1; p is 1; z is an integer from 1 to 7; R is hydrogen; $R_2$ and $R_3$ are each hydrogen; $R_4$ is hydrogen or $C_{1-4}$ alkyl; $G_1$ is a 5-membered heteroaromatic group containing 3 nitrogen atoms, which can optionally be substituted by 1, 2, 3 or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_4$, and combinations of two or more thereof; Y is a moiety selected from the group consisting of phenyl and a 5- or 6-membered heteroaromatic group, either of which can optionally be substituted by Y'; and Y' is phenyl or a 5-6-membered heteroaromatic group which can optionally be substituted by 1 or 2 $R_2$ groups, with the proviso that $G_1$, Y and Y' are not simultaneously phenyl.

In the compound of Formula (I) and Formula (IA), G is aryl or a 5-6 membered heteroaromatic group or 8-11 membered heteroaromatic group, which may be benzofused or optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $C(=O)OR_4$. In embodiments, G is an aryl group. In embodiments, G is a 5-membered heteroaromatic group. In embodiments, G is a 6-membered heteroaromatic group. In embodiments, G is an 8-membered heteroaromatic group. In embodiments, G is an 9-membered heteroaromatic group. In embodiments, G is a 10-membered heteroaromatic group. In embodiments, G is an 11-membered heteroaromatic group.

In the compound of Formula (I) and Formula (IA), W is S, $SO_2$, O, $CHR_2$, or $NR_4$. In embodiments, W is S. In embodiments, W is $SO_2$. In embodiments, W is O. In embodiments W is $CHR_2$. In embodiments, W is $NR_4$.

In the compound of Formula (I) and Formula (IA), n is 0 or 1. In embodiments, n is 0. In embodiments, n is 1.

In the compound of Formula (I) and Formula (IA), m is 1 or 2. In embodiments, m is 1. In embodiments, m is 2.

In the compound of Formula (I) and Formula (IA), p is 0, 1 or 2. In embodiments, p is 1. In embodiments, p is 2. In embodiments, p is 0. In embodiments, p is 1 or 2.

In the compound of Formula (I), q is 0 or 1. In embodiments, q is 0. In embodiments, q is 1. In embodiments, q is 0 and n is 0. In embodiments, q is 1 and p is 0.

In the compound of Formula (I) and Formula (IA), z is an integer ranging from 1 to 7. In embodiments, z is 1. In embodiments, z is 2. In embodiments, z is 3. In embodiments, z is 4. In embodiments, z is 5. In embodiments, z is 6. In embodiments, z is 7.

In the compound of Formula (I) and Formula (IA), R is independently hydrogen or $C_{1-4}$ alkyl. In embodiments, R is hydrogen. In embodiments, R is $C_{1-4}$alkyl.

In the compound of Formula (I) and Formula (IA), $R_1$ is hydrogen, $C_{1-4}$alkyl, or $C_{1-4}$ alkoxy. In embodiments, $R_1$ is hydrogen. In embodiments, $R_1$ is $C_{1-4}$alkyl. In embodiments, $R_1$ is $C_{1-4}$alkoxy.

In the compound of Formula (I) and Formula (IA), $R_2$ is hydrogen, F, $C_{1-4}$alkyl, OH, or $C_{1-4}$ alkoxy. In embodiments, $R_2$ is hydrogen. In embodiments, $R_2$ is fluorine. In embodiments, $R_2$ is $C_{1-4}$alkyl. In embodiments, $R_2$ is OH. In embodiments, $R_2$ is $C_{1-4}$alkoxy.

In the compound of Formula (I) and Formula (IA), $R_3$ is hydrogen, F, $C_{1-4}$alkyl, OH, or $C_{1-4}$ alkoxy. In embodiments, $R_3$ is hydrogen. In embodiments, $R_3$ is fluorine. In embodiments, $R_3$ is $C_{1-4}$alkyl. In embodiments, $R_3$ is OH. In embodiments, $R_3$ is $C_{1-4}$alkoxy.

In the compound of Formula (I) and Formula (IA), $R_4$ is hydrogen or $C_{1-4}$alkyl. In embodiments, $R_4$ is hydrogen. In embodiments, $R_4$ is $C_{1-4}$alkyl.

In the compound of Formula (I) and Formula (IA), $G_1$ is a phenyl group or a 5-6-membered heteroaromatic group or a 8-11 membered heteroaromatic group, any of which groups may be optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_4$. In embodiments, $G_1$ is a phenyl group. In embodiments, $G_1$ is a 5-membered heteroaromatic group. In embodiments, $G_1$ is a 6-membered heteroaromatic group. In embodiments, $G_1$ is an 8-membered heteroaromatic group. In embodiments, $G_1$ is an 9-membered heteroaromatic group. In embodiments, $G_1$ is a 10-membered heteroaromatic group. In embodiments, $G_1$ is an 11-membered heteroaromatic group.

In the compound of Formula (I) and Formula (IA), Y is H or phenyl, or a moiety selected from the group consisting of: 5-6 membered heteroaromatic group, saturated mono 3-7 membered carbocyclic group or 8-11 membered bicyclic carbocyclic group in which one or more atom carbons may be replaced by $NR_4$, O, S; any of which groups may be optionally substituted by one or two substituents selected from: halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $SO_2NH_2$, $C(=O)O_xR_4$ wherein x is 0 or 1, or Y'. In embodiments, Y is H. In embodiments, Y is phenyl. In embodiments, Y is a 5 membered heteroaromatic group. In embodiments, Y is a 6 membered heteroaromatic group. In embodiments, Y is a saturated mono 3-7 membered carbocyclic group. In embodiments, Y is a saturated mono 5-membered carbocyclic group. In embodiments, Y is a saturated mono 6-membered carbocyclic group. In embodiments, Y is an 8-11 membered bicyclic carbocyclic group in which one or more atom carbons may be replaced by $NR_4$, O, S.

In the compound of Formula (I) and Formula (IA), Y' is phenyl, or a 5-6-membered heteroaromatic group optionally substituted by 1 or 2 $R_2$ groups, with the proviso that $G_1$, Y and Y' are not simultaneously phenyl. In embodiments, Y' is phenyl. In embodiments, Y' is a 5-membered heteroaromatic group optionally substituted by 1 or 2 $R_2$ groups, with the proviso that $G_1$, Y and Y' are not simultaneously phenyl. In embodiments, Y' is a 6-membered heteroaromatic group optionally substituted by 1 or 2 $R_2$ groups, with the proviso that $G_1$, Y and Y' are not simultaneously phenyl.

The term "aryl" refers to an aromatic carbocyclic moiety, such as phenyl, biphenyl or naphtyl.

The term "5-6-membered heteroaromatic group" refers to a monocyclic 5- or 6-membered aromatic heterocyclic group containing 1, 2, 3 or 4 heteroatoms, for example from 1 to 3 heteroatoms, selected from O, N and S. When the group contains 2-4 heteroatoms, one may be selected from O, N and S and the remaining heteroatoms may be N. Examples of 5 and 6-membered heteroaromatic groups include pyrrolyl, imidazolyl, pyrazolyl, oxazolyl, isoxazolyl, oxadiazolyl, isothiazolyl, thiazolyl, furyl, thienyl, thiadiazolyl, pyridyl, triazolyl, triazinyl, pyridazinyl, pyrimidinyl and pyrazinyl.

The term "8-11-membered heteroaromatic group" refers to a bicyclic aromatic ring system containing a total of 8, 9, 10, or 11 carbon atoms, wherein 1, 2, 3 or 4 or 5 of the carbon atoms are optionally replaced by a heteroatom independently selected from O, S and N. The term includes bicyclic systems wherein both rings are aromatic, as well as bicyclic ring systems wherein one of the rings is partially or fully saturated. Examples of 8- to 11-membered bicyclic groups wherein both rings are aromatic include indenyl, naphthyl and azulenyl. Examples of 8- to 11-membered bicyclic groups having 1, 2, 3, 4 or 5 heteroatoms, in which both rings are aromatic, include: 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl e.g. benzimidazol-2-yl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl. Examples of 8- to 11-membered bicyclic groups having 1, 2, 3, 4 or 5 heteroatoms, in which one of the rings is partially or fully saturated includes dihydrobenzofuranyl, indanyl, tetrahydronaphthyl, indolinyl, isoindolinyl, tetrahydroisoquinolinyl, tetrahydroquinolyl, benzoxazinyl and benzoazepinyl.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. The term "n-$C_{1-4}$alkyl" refers to the unbranched alkyls as defined above.

The term "$C_{1-4}$alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

The term "saturated mono 3-7 membered carbocyclic group" and the term "8-11 membered bicyclic carbocyclic group" refers to 3 or 4, 5, 6, or 7-membered saturated monocyclic group or 8, 9, 10, 11 membered saturated bicyclic wherein 1, 2, 3, 4 or 5 of the carbon atoms are replaced by a heteroatom independently selected from O, S and $NR_3$ and which is partially or fully saturated. Examples of 3-7 membered carbocyclic group containing heteroatoms which are fully saturated include pyrrolidinyl, imidazolidinyl, pyrazolidinyl, isothiazolyl, thiazolyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl. Examples of "3-7 membered carbocyclic group containing heteroatoms" which are partially saturated 5 or 6-membered monocyclic rings include oxazolinyl, isoaxazolinyl, imidazolinyl, pyrazolinyl, 1,2,3,6-tetrahydropyridyl and 3,6-dihydro-2H-pyranyl. Examples of "8-11 membered bicyclic carbocyclic group" include decahydroquinolinyl, octahydro-2H-1,4-benzoxazinyl, 8-oxabicyclo[3.2.1]octan-3-yl, 8-oxa-3-azabicyclo[3.2.1]octane and octahydro-1H-cyclopenta[b]pyridinyl. Examples of partially saturated "8-11 membered bicyclic rings" include 2,3-dihydro-1H-indolyl, 1,2,3,4-tetrahydroquinolinyl, 1,2,3,4-tetrahydroisoquinolinyl and 2,3,4,5-tetrahydro-1H-3-benzazepinyl.

Any of the groups described herein may be attached to the rest of the molecule at any suitable position, as will be known to the skilled artisan.

The term "pharmaceutically acceptable salt" and "salt" refer to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

Certain of the compounds of the invention may form acid addition salts with one or more equivalents of the acid. The present invention includes within its scope all possible stoichiometric and non-stoichiometric forms.

Certain groups or substituents included in the present invention may be present as isomers. The present invention includes within its scope all such isomers, including racemates, enantiomers, tautomers and mixtures thereof. Certain of the substituted heteroaromatic groups included in the compound of formula (I) or the compounds of formula (IA) may exist in one or more tautomeric forms. The present invention includes within its scope all such tautomeric forms, including mixtures.

Pharmaceutical acceptable salts may also be prepared from other salts, including other pharmaceutically acceptable salts, of the compound of formula (I) or the compound of formula (IA) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of Formula (I) or a compound of Formula (IA), or any of the examples described herein, in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of Formula (I) or compounds of Formula (IA) may exist as polymorphs, which are included in the scope of the present invention.

Those skilled in the art will appreciate that in the preparation of the compounds of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate When a specific enantiomer of a compound of formula (I) or a compound of formula (IA) is required, this may be obtained for example by resolution of a corresponding enantiomeric mixture of a compound of formula (I) or a compound of formula (IA) using conventional methods. Thus the required enantiomer may be obtained from the racemic a compound of formula (I) or a compound of formula (IA) by use of chiral HPLC procedure.

The subject invention also includes isotopically-labelled compounds, which are identical to those recited in a compound of formula (I) or a compound of formula (IA) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and pharmaceutically acceptable salts of the compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

Exemplary compounds of the present invention, and of Formula (I) and Formula (IA), include the following Compound 1 through Compound 38:

Compound 1: 2-(4-fluorophenyl)-4-(3-({[4-methyl-5-(4-methyl-1,3-oxazol-5-yl)-4H-1,2,4-triazol-3-yl]sulfanyl}propyl)morpholine or a pharmaceutically acceptable salt thereof.

Compound 2A: (2S)-2-(4-fluorophenyl)-4-(3-({[4-methyl-5-(4-methyl-1,3-oxazol-5-yl)-4H-1,2,4-triazol-3-yl]sulfanyl}propyl)morpholine or a pharmaceutically acceptable salt thereof Compound 2B: (2R)-2-(4-fluorophenyl)-4-(3-{[4-methyl-5-(4-methyl-1,3-oxazol-5-yl)-4H-1,2,4-triazol-3-yl]sulfanyl)}propyl)morpholine or a pharmaceutically acceptable salt thereof Compound 3A: (2R)-2-(4-fluorophenyl)-4-(3-{[4-methyl-5-(4-methyl-1,3-oxazol-5-yl)-4H-1,2,4-triazol-3-yl]sulfanyl}propyl)morpholine or a pharmaceutically acceptable salt thereof.

Compound 3B: (2S)-2-(4-fluorophenyl)-4-(3-{[4-methyl-5-(4-methyl-1,3-oxazol-5-yl)-4H-1,2,4-triazol-3-yl]sulfanyl}propyl)morpholine or a pharmaceutically acceptable salt thereof.

Compound 4: 4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine or a pharmaceutically acceptable salt thereof.

Compound 5A: (2S)-4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine or a pharmaceutically acceptable salt thereof.

Compound 5B: (2R)-4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine or a pharmaceutically acceptable salt thereof.

Compound 6A: (2R)-4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine or a pharmaceutically acceptable salt thereof.

Compound 6B: (2S)-4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine or a pharmaceutically acceptable salt thereof.

Compound 7: 4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine or a pharmaceutically acceptable salt thereof.

Compound 8A: (2S)-4-(3-({[4-methyl-5-(4-methyl-1,3-oxazol-5-yl)-4H-1,2,4-triazol-3-yl]sulfanyl}propyl)-2-[4-(trifluoromethyl)phenyl]morpholine or a pharmaceutically acceptable salt thereof.

Compound 8B: (2R)-4-(3-({[4-methyl-5-(4-methyl-1,3-oxazol-5-yl)-4H-1,2,4-triazol-3-yl]sulfanyl}propyl)-2-[4-(trifluoromethyl)phenyl]morpholine or a pharmaceutically acceptable salt thereof.

Compound 9A: (2R)-4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine or a pharmaceutically acceptable salt thereof.

Compound 9B: (2S)-4-(3-({[4-methyl-5-(4-methyl-1,3-oxazol-5-yl)-4H-1,2,4-triazol-3-yl]sulfanyl}propyl)-2-[4-(trifluoromethyl)phenyl]morpholine or a pharmaceutically acceptable salt thereof.

Compound 10A: (2R)-4-(3-({[4-methyl-5-(4-methyl-1,3-oxazol-5-yl)-4H-1,2,4-triazol-3-yl]sulfanyl}propyl)-2-[4-(trifluoromethyl)phenyl]morpholine hydrochloride.

Compound 10B: (2R)-4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine or a pharmaceutically acceptable salt thereof.

Compound 10C: (2S)-4-(3-({[4-methyl-5-(4-methyl-1,3-oxazol-5-yl)-4H-1,2,4-triazol-3-yl]sulfanyl}propyl)-2-[4-(trifluoromethyl)phenyl]morpholine hydrochloride.

Compound 10D: (2S)-4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine or a pharmaceutically acceptable salt thereof.

Compound 11: 4-{4-methyl-5-[(3-{2-[4-(trifluoromethyl)phenyl]-morpholin-4-yl}propyl)sulfanyl]-4H-1,2,4-triazol-3-yl}benzamide or a pharmaceutically acceptable salt thereof.

Compound 12A: 4-[4-methyl-5-({(3-[(2S)-2-[4-(trifluoromethyl)phenyl]morpholine-4-yl]propyl}sulfanyl)-4H-1,2,4-triazol-3-yl]benzamide or a pharmaceutically acceptable salt thereof.

Compound 12B: 4-[4-methyl-5-({3-[(2R)-2-[4-(trifluoromethyl)phenyl]morpholine-4-yl]propyl}sulfanyl)-4H-1,2,4-triazol-3-yl]benzamide or a pharmaceutically acceptable salt thereof.

Compound 13A: 4-[4-methyl-5-({3-[(2R)-2-[4-(trifluoromethyl)phenyl]morpholin-4-yl]propyl}sulfanyl)-4H-1,2,4-triazol-3-yl]benzamide or a pharmaceutically acceptable salt thereof.

Compound 13B: 4-[4-methyl-5-({3-[(2S)-2-[4-(trifluoromethyl)phenyl]-morpholine-4-yl]propyl}sulfanyl)-4H-1,2,4-triazol-3-yl]benzamide or a pharmaceutically acceptable salt thereof.

Compound 14: 4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine or a pharmaceutically acceptable salt thereof.

Compound 15A: (2S)-4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine or a pharmaceutically acceptable salt thereof.

Compound 15B: (2R)-4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine or a pharmaceutically acceptable salt thereof.

Compound 16A: (2R)-4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine or a pharmaceutically acceptable salt thereof.

Compound 16B: (2S)-4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine or a pharmaceutically acceptable salt thereof.

Compound 17: 4-(3-({[4-methyl-5-(pyridin-4-yl)-4H-1,2,4-triazol-3-yl]sulfanyl}propyl)-2-[4-(trifluoromethyl)phenyl]morpholine or a pharmaceutically acceptable salt thereof Compound 18: 4-(3-{[4-methyl-5-(pyridin-3-yl)-4H-1,2,4-triazol-3-yl]sulfanyl}propyl)-2-[4-(trifluoromethyl)phenyl]morpholine or a pharmaceutically acceptable salt thereof.

Compound 19: 4-(3-{[4-methyl-5-(pyrazin-2-yl)-4H-1,2,4-triazol-3-yl]sulfanyl}propyl)-2-[4-(trifluoromethyl)phenyl]morpholine or a pharmaceutically acceptable salt thereof.

Compound 20: 5-{4-methyl-5-[(3-{2-[4-(trifluoromethyl)phenyl]morpholin-4-yl}propyl)sulfanyl]-4H-1,2,4-triazol-3-yl}pyridine-2-carboxamide or a pharmaceutically acceptable salt thereof.

Compound 21: 4-[3-({4-methyl-5-[4-(4H-1,2,4-triazol-4-yl)phenyl]-4H-1,2,4-triazol-3-yl}sulfanyl)propyl]-2-[4-(trifluoromethyl)phenyl]morpholine or a pharmaceutically acceptable salt thereof.

Compound 22: 6-{4-methyl-5-[(3-{2-[4-(trifluoromethyl)phenyl]morpholin-4-yl}propyl)sulfanyl]-4H-1,2,4-triazol-3-yl}pyridine-3-carboxamide or a pharmaceutically acceptable salt thereof.

Compound 23: 3-{4-methyl-5-[(3-{2-[4-(trifluoromethyl)phenyl]morpholin-4-yl}propyl)sulfanyl]-4H-1,2,4-triazol-3-yl}benzamide or a pharmaceutically acceptable salt thereof.

Compound 24: 4-(3-({[4-methyl-5-(1-methyl-1H-pyrrol-2-yl)-4H-1,2,4-triazol-3-yl]sulfanyl}propyl)-2-[4-(trifluoromethyl)phenyl]morpholine or a pharmaceutically acceptable salt thereof.

Compound 25: 4-{3-[(5-cyclohexyl-4-methyl-4H-1,2,4-triazol-3-yl)sulfanyl]propyl}-2-[4-(trifluoromethyl)phenyl]morpholine or a pharmaceutically acceptable salt thereof.

Compound 26: 4-(3-{[4-methyl-5-(1,3-thiazol-2-yl)-4H-1,2,4-triazol-3-yl]sulfanyl}propyl)-2-[4-(trifluoromethyl)phenyl]morpholine or a pharmaceutically acceptable salt thereof.

Compound 27: 4-(3-{[4-methyl-5-(1-methyl-1H-pyrazol-5-yl)-4H-1,2,4-triazol-3-yl]sulfanyl}propyl)-2-[4-(trifluoromethyl)phenyl]morpholine or a pharmaceutically acceptable salt thereof.

Compound 28: 4-(3-({[4-methyl-5-(thiophen-3-yl)-4H-1,2,4-triazol-3-yl]sulfanyl}propyl)-2-[4-(trifluoromethyl)phenyl]morpholine or a pharmaceutically acceptable salt thereof.

Compound 29: 4-[3-({4-methyl-5-[4-(1,3,4-oxadiazol-2-yl)phenyl]-4H-1,2,4-triazol-3-yl}sulfanyl)propyl]-2-[4-(trifluoromethyl)phenyl]morpholine or a pharmaceutically acceptable salt thereof.

Compound 30: 4-[3-({4-methyl-5-[4-(5-methyl-1,2,4-oxadiazol-3-yl)phenyl]-4H-1,2,4-triazol-3-yl}sulfanyl)propyl]-2-[4-(trifluoromethyl)phenyl]morpholine or a pharmaceutically acceptable salt thereof.

Compound 31: 4-{4-methyl-5-[(3-{2-[4-(trifluoromethyl)phenyl]morpholin-4-yl}propyl)sulfanyl]-4H-1,2,4-triazol-3-yl}benzonitrile or a pharmaceutically acceptable salt thereof Compound 32: 1-(4-{4-methyl-5-[(3-{2-[4-(trifluoromethyl)phenyl]morpholine-4-yl}propyl)sulfanyl]-4H-1,2,4-triazol-3-yl}phenyl)ethan-1-one or a pharmaceutically acceptable salt thereof.

Compound 33: 4-{4-methyl-5-[(3-{2-[4-(trifluoromethyl)phenyl]morpholine-4-yl}propyl)sulfanyl]-4H-1,2,4-triazol-3-yl}benzene-1-sulfonamide or a pharmaceutically acceptable salt thereof.

Compound 34: 2-[2-fluoro-4-(trifluoromethyl)phenyl]-4-(3-{[4-methyl-5-(4-methyl-1,3-oxazol-5-yl)-4H-1,2,4-triazol-3-yl]sulfanyl})propyl)morpholine or a pharmaceutically acceptable salt thereof.

Compound 35: 4-{5-[(3-{2-[2-fluoro-4-(trifluoromethyl)phenyl]morpholin-4-yl}propyl)sulfanyl]-4-methyl-4H-1,2,4-triazol-3-yl)}benzamide or a pharmaceutically acceptable salt thereof.

Compound 36: 4-(3-{[4-methyl-5-(4-methyl-1,3-oxazol-5-yl)-4H-1,2,4-triazol-3-yl]sulfanyl}propyl)-2-(4-methylphenyl)morpholine or a pharmaceutically acceptable salt thereof.

Compound 37: 4-[3-({4-methyl-5-[4-(5-methyl-1,2,4-oxadiazol-3-yl)phenyl]-4H-1,2,4-triazol-3-yl}sulfanyl)propyl]-2-(4-methylphenyl)morpholine or a pharmaceutically acceptable salt thereof.

Compound 38: 2-(4-bromophenyl)-4-(3-{[4-methyl-5-(4-methyl-1,3-oxazol-5-yl)-4H-1,2,4-triazol-3-yl]sulfanyl}propyl)morpholine or a pharmaceutically acceptable salt thereof.

The present invention also provides a process for preparing a compound of formula (I), a compound of formula (IA), and salts thereof as defined above. The process of the present invention for preparing compounds of formula (I) and compounds of formula (IA) comprises the steps of:

(a) reacting a compound of formula (II):

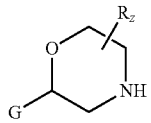

(II)

wherein G, R and z are as defined for formula (I) or formula (IA),
with a compound of formula (III):

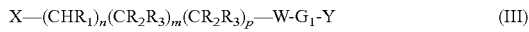

(III)

wherein $R_1$, $R_2$, $R_3$, n, m, p, W, $G_1$ and Y are as defined for formula (I) or formula (IA), and X is a leaving group or an aldehyde, and thereafter optionally for process (a): (i) removing any protecting group(s); and/or (ii) forming a salt; and/or (iii) converting a compound of formula (I) or a salt thereof to another compound of formula (I) or a salt thereof, or a compound of formula (IA) or a salt thereof.

Process (a) may be performed using conventional methods for the formation of a tertiary amine. When X is a leaving group, it can be halogen such as chlorine. Alternatively X can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When X is an halogen the reaction may be carried out using a base such as sodium carbonate in the presence of a source of iodide such as sodium iodide in a solvent such as N,N-dimethylformamide at a suitable temperature, e.g. 60° C. When X is an aldehyde the reaction may be carried out using a reducing agent such as sodium triacetoxyborohydride in a suitable solvent such as dichloromethane or acetonitrile optionally in the presence of acetic acid or a Lewis acid in a catalytic amount and at a suitable temperature such as room temperature.

In one aspect of the present invention there is provided synthetic processes for the preparation of compounds of formula (II) in which R is hydrogen. Compounds of formula (IX), corresponding to compounds of formula (II) in which R is hydrogen may be synthesized by a process comprising the following Scheme 1:

Scheme 1

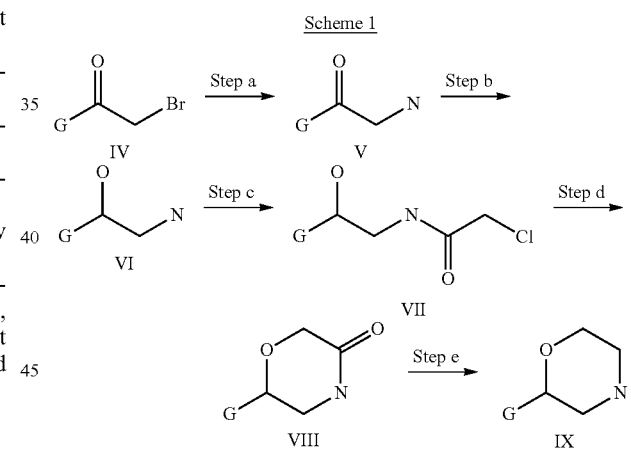

wherein: Step a means conversion of bromide into an aminic function to provide the corresponding α-aminoketone (V); Step b means the reduction of carbonylic function to give the aminoalchol (VI); Step c means acylation of aminoalchool (VI) to give compounds of formula (VII); Step d means ring closure of (VII) via intramolecular nucleophilic substitution to provide the morpholinone (VIII); and Step e means reduction of the morpholinone (VIII) to give compounds of formula (IX).

Step a may be effected treating the bromo derivative (IV) with an appropriate source of nitrogen as for example Hexamethylenetetramine (HMTA) in a suitable solvent, such as chloroform, at an appropriate temperature, such as room temperature. This is followed by treating the formed intermediate with acidic conditions, such as in the presence of hydrochloric acid, allowing time to react as appropriate and a suitable workup. Alternatively, the bromo derivative (IV) may be reacted with sodium diformylamide in a suitable solvent, such as acetonitrile, and at a temperature ranging from room temperature to 70° C. Analogously, this is followed by treating the formed intermediate with acidic conditions, such as in the presence of hydrochloric acid, at an appropriate temperature, such as reflux temperature, and allowing time to react as appropriate.

Step b can be performed using a suitable reducing agent in a compatible solvent, such as sodium borohydride in methanol, at an appropriate temperature, such as for example 0° C. This is followed by a suitable workup.

Step c consists of acylation of aminoalchool (VI) with the appropriate acylchloride using either Shotten-Bauman conditions, such as for example partitioning the aminoalchol between an organic solvent such as dichloromethane and an alkaline aqueous solution such as aqueous solution of sodium hydroxide, followed by slow addition of the acylchloride at an appropriate temperature such as 0° C. Alternatively, the acylation may be performed in an organic solvent such as dichloromethane in the presence of an organic base such as triethylamine and at an appropriate temperature such as 0° C. This is followed by allowing time to react as appropriate and a suitable workup.

Step d may be performed using a suitable base in a compatible solvent, such as sodium ter-butoxide in THF, at an appropriate temperature, such as a temperature ranging from 0° C. to room temperature. This is followed by allowing time to react and a suitable workup.

Step e can be performed using a suitable reducing agent in a compatible solvent, such as Lithium aluminium hydride 1M solution in THF, at an appropriate temperature, such as a temperature ranging from 0° C. to reflux. This is followed by allowing time to react and a suitable workup.

A compound of formula (III) may itself be prepared by reacting a compound of formula (X):

W-G$_1$-Y    (X)

wherein G$_1$ and Y are as hereinbefore defined with a compound of formula (XI):

X—(CHR$_1$)$_n$(CR$_2$R$_3$)$_m$(CR$_2$R$_3$)$_p$-L    (XI)

wherein X is defined as for formula (III) and L is a leaving group, e.g., a bromine atom. For typical reaction conditions, see Preparation 3 hereinafter.

A compound of formula (I) or a compound of formula (IA), wherein W is SO or SO$_2$, may itself be prepared by (a) reacting a compound of formula (XII):

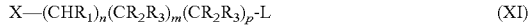
S-G$_1$-Y    (XII).

wherein G$_1$ and Y are as hereinbefore defined and S is a sulphur atom with a compound of formula (XI):

X—(CHR$_1$)$_n$(CR$_2$R$_3$)$_m$(CR$_2$R$_3$)$_p$-L    (XI).

wherein X is defined as for formula (III) and L is a leaving group, e.g., a bromine atom, and oxidizing the sulphur with an appropriate oxidizing agent such as oxone or m-chloroperbenzoic acid in a suitable solvent such as dichloromethane.

Compounds of formula (I) or formula (IA) wherein W is oxygen and G, R, R$_1$, R$_2$, R$_3$, n, m, p, z, G$_1$ and Y are as defined as above, may be prepared by reacting a compound of formula

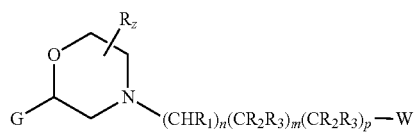
(XIII)

wherein G, R, R$_1$, R$_2$, R$_3$, n, m, p and z are as defined for formula (I), with a compound of formula (XIV):

X-G$_1$-Y    (XIV).

wherein G$_1$ and Y are as hereinbefore defined and X is a leaving group such as methyl sulphone.

Interconversion reactions between compounds of formula (I) and compounds of formula (IA) and salts thereof may be performed using methods well known in the art.

Compounds of formula (I) and compounds of formula (IA) have been found to exhibit affinity for dopamine receptors, in particular the D$_3$ receptor, and are expected to be useful in the treatment of disease states which require modulation of such receptors, such as psychotic conditions. Such affinity is typically calculated from the IC$_{50}$ as the concentration of a compound necessary to displace 50% of the radiolabeled ligand from the receptor, and is reported as a "K$_i$" value calculated by the following equation:

$$K_i = \frac{IC_{50}}{1 + L/K_D}$$

where L=radioligand and K$_D$=affinity of radioligand for receptor (Cheng and Prusoff, Biochem. Pharmacol. 22:3099, 1973).

In the context of the present invention pKi (corresponding to the antilogarithm of Ki) is used instead of Ki and the compounds of the present invention typically show pKi greater than 6. In one aspect the present invention provides compounds of formula (I) and compounds of formula (IA) having a pKi comprised between 6 and 7. In another aspect the present invention provides compounds of formula (I) and compounds of formula (IA) having a pKi comprised between 7 and 8. In a further aspect the present invention provides compounds of formula (I) and compounds of formula (IA) having a pKi greater than 8.

The compounds of formula (I) and compounds of formula (IA) have also been found to have greater affinity for dopamine D$_3$ than for D$_2$ receptors. The therapeutic effect of currently available antipsychotic agents (neuroleptics) is generally believed to be exerted via blockade of D$_2$ receptors; however this mechanism is also thought to be responsible for undesirable extrapyramidal side effects (eps) associated with many neuroleptic agents. It has been suggested that blockade of the recently characterized dopamine D$_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of the present invention are provided which have higher (e.g. ≥10× or ≥100× higher) affinity for dopamine D$_3$ than dopamine D$_2$ receptors (such affinity can be measured using standard methodology for example using cloned dopamine receptors—see herein). Said compounds may suitably be used as selective modulators of D$_3$ receptors.

From the localization of D$_3$ receptors, the compounds of the invention have utility for the treatment of substance abuse (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, premature ejaculation, sleep disorders, emesis, movement disorders, obsessive-compulsive disorders, amnesia, aggression, autism, vertigo, dementia, circadian rhythm disorders and gastric motility disorders e.g. IBS. In embodiments, the compounds of formula (I) and the compounds of formula (IA) and any one of Compounds 1-38 provide for methods of treating alcohol abuse, alcohol dependence, or alcohol relapse. In embodiments, the compounds of Formula (I), the compounds of formula (IA), and any one of Compounds 1-38 provide for methods of treating opioid abuse, opioid dependence, or opioid relapse. In embodiments, the compounds of Formula (I), the compounds of formula (IA), and any one of Compounds 1-38 provide for methods of treating dyskinetic disorders. In embodiments, the compounds of Formula (I), the compounds of formula (IA), and any one of Compounds 1-38 provide for methods of treating obsessive-compulsive disorder.

Compounds of formula (I), compounds of formula (IA), and any one of Compounds 1-38 may be used for treatment of all aspects of drug dependency including withdrawal symptoms from drugs of abuse such as alcohol, cocaine, opioids, nicotine, benzodiazepines and inhibition of tolerance induced by opioids. In addition, compounds of formula (I), compounds of formula (IA), and pharmaceutically acceptable salts and solvates thereof may be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

The compounds of formula (I), compounds of formula (IA), and any one of Compounds 1-38 can be used as antipsychotic agents for example in the treatment of schizophrenia, schizoaffective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242).

Within the context of the present invention, the terms describing the indications used herein are classified in the Diagnostic and Statistical Manual of Mental Disorders, 4th Edition, published by the American Psychiatric Association (DSM-V). The various subtypes of the disorders mentioned herein are contemplated as part of the present invention.

The term "schizophrenia" includes: Schizotypal (personality disorder; Delusional Disorder; Brief Psychotic Disorder; Schizopreniform Disorder; Schizophrenia; Schizoaffective Disorder; Substance/Medication-Induced Psychotic Disorder; Psychotic Disorder due to another Medical Condition.

The term "obsessive-compulsive disorder" includes: Obsessive Compulsive Disorder; Body Dismorphic Disorder; Hoarding Disorder; Trichotillomania (Hair-Pulling Disorder); Excoriation (Skin-Picking) Disorder; Substance/Medication-Induced Obsessive-Compulsive and Related Disorder; Obsessive-Compulsive and Related Duisorder due to Another Medical Condition; Other Specified Obsessive-Compulsive and Related Disorders; Unspecified Obsessive-Compulsive and Related Disorders. The obsessive-compulsive disorder can be compulsive gambling.

The term "substance-related disorders and addictive disorders" includes: Substance-Related Disorders such as Substance Use Disorders; Substance-Induced Disorders; Substance Intoxication and Withdrawal; Substance/Medication-Induced Mental Disorders; Alcohol-Related Disorders such as Alcohol Use Disorder: Alcohol Intoxication; Alcohol Withdrawal; Other Alcohol-Induced Disorders; Unspecified Alcohol-Related Disorders; Caffeine-Related Disorders such as Caffeine Intoxication; Caffeine Withdrawal; Other Caffeine-Induced Disorders; Unspecified Caffeine-Related Disorders; Cannabis-Related Disorders such as Cannabis Use Disorder; Cannabis Intoxication; Cannabis Withdrawal; Other Cannabis-Induced Disorders; Unspecified Cannabis-Related Disorders; Hallucinogen-Related Disorders such as Phencyclidine Use Disorder; Other Hallucinogen Use Disorder; Phencyclidine Intoxication; Other Hallucinogen Intoxication; Hallucinogen Persisting Perception Disorder; Other Phencyclidine-Induced Disorders; Other Hallucinogen-Induced Disorders Unspecified Phencyclidine-Related Disorders; Unspecified Hallucinogen-Related Disorders; Inhalant-Related Disorders such as Inhalant Use Disorder; Inhalant Intoxication; Other Inhalant-Induced Disorders; Unspecified Inhalant-Related Disorders; Opioid-Related Disorders such as Opioid Use Disorder; Opioid Intoxication; Opioid Withdrawal; Other Opioid-Induced Disorders; Unspecified Opioid-Related Disorders; Sedative-, Hypnotic-, or Anxiolytic-Related Disorders such as Sedative-, Hypnotic-, or Anxiolytic Use Disorder; Sedative-, Hypnotic-, or Anxiolytic Intoxication; Sedative-, Hypnotic-, or Anxiolytic Withdrawal; Other Sedative-, Hypnotic-, or Anxiolytic-Induced Disorders; Unspecified Sedative-, Hypnotic-, or Anxiolytic-Related Disorders; Stimulant-Related Disorders such as Stimulant Use Disorder; Stimulant Intoxication; Stimulant Withdrawal; Other Stimulant-Induced Disorders; Unspecified Stimulant-Related Disorders; Tobacco-Related Disorders such as Tobacco Use Disorder; Tobacco Intoxication; Tobacco Withdrawal; Other Tobacco-Induced Disorders; Unspecified Tobacco-Related Disorders; Other (or Unknown) Substance-Related Disorders such as Other (or Unknown) Substance Use Disorder; Other (or Unknown) Substance Intoxication; Other (or Unknown) Substance Withdrawal; Other (or Unknown) Substance-Induced Disorders; Unspecified Other (or Unknown) Substance-Related Disorders.

In a further aspect therefore the present invention provides a method of treating a condition for which modulation (especially antagonism/inhibition) of dopamine $D_3$ receptors is beneficial, which comprises administering to a mammal (e.g. human) in need thereof an effective amount of a compound of formula (I), a compound of formula (IA), or a pharmaceutically (i.e physiologically) acceptable salt thereof. Such conditions in particular include psychoses/psychotic conditions such as schizophrenia, and substance abuse, such as opioid dependency.

The invention also provides the use of a compound of formula (I), a compound of formula (IA), or a pharmaceutically acceptable salt thereof in the manufacture of a medicament for the treatment of a condition in a mammal for which modulation (especially antagonism/inhibition) of dopamine $D_3$ receptors is beneficial. The invention also provides a compound of formula (I), a compound of formula (IA), or a pharmaceutically acceptable salt thereof for use in the treatment of a condition in a mammal for which modulation (especially antagonism/inhibition) of dopamine $D_3$ receptors is beneficial. In one embodiment, $D_3$ antagonists according to the present invention are used in the treatment of psychoses such as schizophrenia or in the treatment of substance abuse.

Thus, a still further aspect the invention provides a method of treating a psychotic condition (e.g. schizophrenia) or substance abuse which comprises administering to a mammal (e.g. human) in need thereof an effective amount of a compound of formula (I) or a compound of formula (IA) as herein defined or a pharmaceutically acceptable salt thereof.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I), a compound of formula (IA) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges. A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include film, wafers, tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule. Each dosage unit for oral administration contains for example from 1 to 250 mg (and for parenteral administration contains for example from 0.1 to 25 mg) of a compound of the formula (I), a compound of formula (IA), or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

EMBODIMENTS

Embodiment 1

A compound of formula (I) or a pharmaceutically acceptable salt thereof:

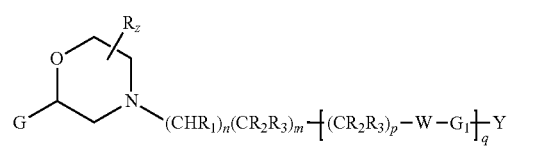

(I)

wherein: G is aryl or a 5-6 membered heteroaromatic group or 8-11 membered heteroaromatic group, which may be benzofused or optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$ alkyl, $C_{1-4}$alkoxy, halo$C_{1-4}$alkoxy, $C_{1-4}$alkanoyl, $SF_5$, $C(=O)NH_2$, $C(=O)OR_4$; W is S, $SO_2$, O, $CHR_2$, $NR_4$; n is 0 or 1; m is 1 or 2; p is 0, 1 or 2; q is 0 or 1; z is an integer ranging from 1 to 7; R is independently hydrogen or $C_{1-4}$alkyl; $R_1$ is hydrogen, $C_{1-4}$alkyl; $C_{1-4}$alkoxy; $R_2$ is hydrogen, F, $C_{1-4}$alkyl; OH, $C_{1-4}$alkoxy; $R_3$ is hydrogen, F, $C_{1-4}$alkyl; OH, $C_{1-4}$alkoxy; $R_4$ is hydrogen, $C_{1-4}$alkyl; $G_1$ is a phenyl group or a 5-6-membered heteroaromatic group or a 8-11 membered heteroaromatic group, any of which groups may be optionally substituted by 1, 2, 3 or 4 substituents selected from the group consisting of: halogen, cyano, hydroxyl, amino, $C_{1-4}$alkylamino, $C_{1-4}$alkyl, haloC$_{1-4}$alkyl, $C_{1-4}$alkoxy, $C_{1-4}$alkanoyl, SF$_5$, C(=O)NH$_2$, C(=O)OR$_4$; Y is H or a moiety selected from the group consisting of: 5-6 membered heteroaromatic group, saturated mono 3-7 membered carbocyclic group or 8-11 membered bicyclic carbocyclic group in which one or more atom carbons may be replaced by NR$_4$, O, S; any of which groups may be optionally substituted by one or two substituents selected from: halogen, cyano, hydroxyl, amino, $C_{1-4}$alkylamino, $C_{1-4}$alkyl, haloC$_{1-4}$alkyl, $C_{1-4}$alkoxy, haloC$_{1-4}$alkoxy, $C_{1-4}$alkanoyl, SF$_5$, C(=O)NH$_2$, SO$_2$NH$_2$, C(=O)O$_x$R$_4$ wherein x is 0 or 1, or Y'; and Y' is phenyl, or a 5-6-membered heteroaromatic group optionally substituted by 1 or 2 $R_2$ groups; with the proviso that n is 0 when q is 0.

Embodiment 2

A compound of formula (IA) or a pharmaceutically acceptable salt thereof:

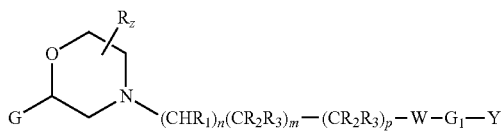

(IA)

wherein: G is aryl or a 5-6 membered heteroaromatic group, either of which can optionally be substituted by 1, 2, 3 or 4 substituents selected from the group consisting of halogen, cyano, hydroxyl, amino, $C_{1-4}$alkylamino, $C_{1-4}$alkyl, haloC$_{1-4}$alkyl, $C_{1-4}$alkoxy, haloC$_{1-4}$alkoxy, $C_{1-4}$alkanoyl, SF$_5$, C(=O)NH$_2$, C(=O)OR$_4$, and combinations of two or more thereof; W is S, SO$_2$, O, CHR$_2$, or NR$_4$; n is 0 or 1; m is 1 or 2; p is 1 or 2; z is an integer from 1 to 7; R is independently hydrogen or $C_{1-4}$alkyl; $R_1$ is hydrogen, $C_{1-4}$alkyl, or $C_{1-4}$alkoxy; $R_2$ and $R_3$ are each independently hydrogen, F, $C_{1-4}$alkyl, OH, or $C_{1-4}$alkoxy; $R_4$ is hydrogen or $C_{1-4}$alkyl; $G_1$ is a phenyl group or a 5-6-membered heteroaromatic group, either of which can optionally be substituted by 1, 2, 3 or 4 substituents selected from the group consisting of halogen, cyano, hydroxyl, amino, $C_{1-4}$alkylamino, $C_{1-4}$alkyl, haloC$_{1-4}$alkyl, $C_{1-4}$alkoxy, $C_{1-4}$alkanoyl, SF$_5$, C(=O)NH$_2$, C(=O)OR$_4$, and combinations of two or more thereof; Y is a moiety selected from the group consisting of phenyl, a 5-6 membered heteroaromatic group, an saturated mono 3-7 membered carbocyclic group; any of which groups may be optionally substituted by one or two substituents selected from: halogen, cyano, hydroxyl, amino, $C_{1-4}$alkylamino, $C_{1-4}$alkyl, haloC$_{1-4}$alkyl, $C_{1-4}$alkoxy, haloC$_{1-4}$alkoxy, $C_{1-4}$alkanoyl, SF$_5$, C(=O)NH$_2$, SO$_2$NH$_2$, C(=O)O$_x$R$_4$ wherein x is 0 or 1, or Y'; and Y' is phenyl, or a 5-6-membered heteroaromatic group optionally substituted by 1 or 2 $R_2$ groups, with the proviso that $G_1$, Y and Y' are not simultaneously phenyl.

Embodiment 3

The compound of Embodiment 2, wherein G is aryl which can optionally be substituted by 1 or 2 substituents selected from the group consisting of halogen, cyano, hydroxyl, amino, $C_{1-4}$alkylamino, $C_{1-4}$alkyl, haloC$_{1-4}$alkyl, $C_{1-4}$alkoxy, haloC$_{1-4}$alkoxy, $C_{1-4}$alkanoyl, SF$_5$, C(=O)NH$_2$, C(=O)OR$_4$, and combinations thereof; W is S; n is 1; m is 1; p is 1; z is an integer from 1 to 7; R is hydrogen; $R_2$ and $R_3$ are each hydrogen; $R_4$ is hydrogen or $C_{1-4}$alkyl; $G_1$ is a 5-membered heteroaromatic group containing 3 nitrogen atoms, which can optionally be substituted by 1, 2, 3 or 4 substituents selected from the group consisting of halogen, cyano, hydroxyl, amino, $C_{1-4}$alkylamino, $C_{1-4}$alkyl, haloC$_{1-4}$ alkyl, $C_{1-4}$alkoxy, $C_{1-4}$alkanoyl, SF$_5$, C(=O)NH$_2$, C(=O)OR$_4$, and combinations of two or more thereof; Y is a moiety selected from the group consisting of phenyl and a 5- or 6-membered heteroaromatic group, either of which can optionally be substituted by Y'; and Y' is phenyl or a 5-6-membered heteroaromatic group which can optionally be substituted by 1 or 2 $R_2$ groups, with the proviso that $G_1$, Y and Y' are not simultaneously phenyl.

Embodiment 4

Compounds 1-38.

Embodiment 5

A compound according to anyone of Embodiments 1-4 for use as a medicament.

Embodiment 6

A compound according to anyone of Embodiments 1-4 for the use in the treatment of a condition for which modulation of dopamine $D_3$ receptors is beneficial.

Embodiment 7

A compound according to anyone of Embodiments 1-4 for the use in the treatment of a psychosis or a psychotic condition.

Embodiment 8

A compound according to anyone of Embodiments 1-4 for the use in the treatment of schizophrenia.

Embodiment 9

A compound according to anyone of Embodiments 1-4 for the use in the treatment of substance abuse or substance dependence or substance relapse.

Embodiment 10

A compound according to anyone of Embodiments 1-4 for the use in the treatment of a opioid dependence.

Embodiment 11

A method for treating a dopamine $D_3$ receptor disease in a patient in need thereof, the method comprising administering a therapeutically effective amount of a compound according to anyone of Embodiments 1-4 to the patient to treat the disease.

Embodiment 12

A method of treating a psychosis or a psychotic condition in a patient in need thereof, the method comprising administering a therapeutically effective amount of a compound according to anyone of Embodiments 1-4 to the patient to treat the psychosis or the psychotic condition.

Embodiment 13

A method of treating schizophrenia in a patient in need thereof, the method comprising administering a therapeutically effective amount of a compound according to anyone of Embodiments 1-4 to the patient to treat the schizophrenia.

Embodiment 14

A method of substance abuse or substance dependence or substance relapse in a patient in need thereof, the method comprising administering a therapeutically effective amount of a compound according to anyone of Embodiments 1-4 to the patient to treat the substance abuse or substance dependence or substance relapse, respectively.

Embodiment 15

A method of treating opioid dependence in a patient in need thereof, the method comprising administering a therapeutically effective amount of a compound according to anyone of Embodiments 1-4 to the patient to treat the opioid dependence.

Embodiment 16

A pharmaceutical composition comprising a compound of any one of Embodiments 1-4 and a pharmaceutically acceptable excipient.

Embodiment 17

A pharmaceutical composition of Embodiment 16 for the use in the treatment of a condition for which modulation of dopamine $D_3$ receptors is beneficial.

Embodiment 18

A pharmaceutical composition of Embodiment 16 for the use in the treatment of a psychosis or a psychotic condition.

Embodiment 19

A pharmaceutical composition of Embodiment 16 for the use in the treatment of schizophrenia.

Embodiment 20

A pharmaceutical composition of Embodiment 16 for the use in the treatment of substance abuse or substance dependence or substance relapse.

Embodiment 21

A pharmaceutical composition of Embodiment 16 for the use in the treatment of a opioid dependence.

Embodiment 22

A method for treating a dopamine $D_3$ receptor disease in a patient in need thereof, the method comprising administering a therapeutically effective amount of a pharmaceutical composition of Embodiment 16 to the patient to treat the disease.

Embodiment 23

A method of treating a psychosis or a psychotic condition in a patient in need thereof, the method comprising administering a therapeutically effective amount of a pharmaceutical composition of Embodiment 16 to the patient to treat the psychosis or the psychotic condition.

Embodiment 24

A method of treating schizophrenia in a patient in need thereof, the method comprising administering a therapeutically effective amount of a pharmaceutical composition of Embodiment 16 to the patient to treat the schizophrenia.

Embodiment 25

A method of substance abuse or substance dependence or substance relapse in a patient in need thereof, the method comprising administering a therapeutically effective amount of a pharmaceutical composition of Embodiment 16 to the patient to treat the substance abuse or substance dependence or substance relapse, respectively.

Embodiment 26

A method of treating opioid dependence in a patient in need thereof, the method comprising administering a therapeutically effective amount of a pharmaceutical composition of Embodiment 16 to the patient to treat the opioid dependence.

EXAMPLES

The invention is further illustrated by the following non-limiting examples.

In the procedures that follow, after each starting material, reference to a Preparation or Example by number is typically provided. This is provided merely for assistance to the skilled chemist. The starting material may not necessarily have been prepared from the batch referred to.

Were reference is made to the use of a "similar or analogous or as" procedure, as will be appreciated by those skilled in the art, such procedure may involve minor variation, for example reaction temperature, reagent/solvent amount, reaction time, work-up conditions or chromatographic purification conditions.

All temperatures refer to ° C.

Proton Magnetic Resonance (NMR) spectra may be typically recorded either on Varian instruments at 400 or 500 MHz, or on a Bruker instrument at 400 MHz.

Chemical shifts are expressed in parts of million (ppm, δ units). Chemical shifts are reported in ppm downfield (δ) from $Me_4Si$, used as internal standard, and are typically assigned as singlets (s), broad singlets (br.s.), doublets (d), doublets of doublets (dd), doublets of doublets of doublets (ddd), doublets of triplets (dt), triplets (t), triplets of doublets (td), quartets (q), or multiplets (m).

LCMS may be recorded under the following conditions: DAD chromatographic traces, mass chromatograms and mass spectra may be taken on UPLC/PDA/MS Acquity™ system coupled with Micromass ZQ™ or Waters SQD single quadrupole mass spectrometer operated in positive and/or negative ES ionisation mode. The QC methods used were two, one operated under low pH conditions and another one operated under high pH conditions. Details of the method operated under low pH conditions were: column, Acquity BEH C$_{18}$, 1.7 μm, 2.1×50 mm or Acquity CSH C$_{18}$, 1.7 μm, 2.1×50 mm, the temperature column was 40° C.; mobile phase solvent A was milliQ water+0.1% HCOOH, mobile phase solvent B MeCN+0.1% HCOOH. The flow rate was 1 ml/min. The gradient table was t=0 min 97% A-3% B, t=1.5 min 0.1% A-99.9% B, t=1.9 min 0.1% A-99.9% B and t=2 min 97% A-3% B. The UV detection range was 210-350 nm and the ES$^+$/ES$^-$ range was 100-1000 amu.

Details of the method operated under high pH conditions were the same of those listed above for the low pH method apart from: column Acquity BEH C$_{18}$, 1.7 μm, 2.1×50 mm; mobile phase solvent A was 10 mM acqueous solution of NH$_4$HCO$_3$ adjusted to pH=10 with ammonia, mobile phase solvent B MeCN.

Semipreparative mass directed autopurifications (MDAP) were carried out using Waters Fractionlynx™ systems operated under low or high pH chromatographic conditions. The stationary phases used were, XTerra C18, XBridge C18, Sunfire C18, XSelect C18, Gemini AXIA C18. The length of the columns was 5, 10 or 15 cm, while the internal diameter was 19, 21 or 30 mm. The particle size of the stationary phases was 5 or 10 μm. The purifications were carried out using low pH or high pH chromatographic conditions. The mobile phase solvent composition was the same used for QC analysis. The combinations stationary/mobile phases used were: XTerra, XBridge, Sunfire, XSelect—low pH mobile phases and XTerra, XBridge, Gemini AXIA—high pH mobile phases. All the purifications were carried out with the column kept at room T. The flow rate used was 17 or 20 ml/min for columns of internal diameter 19 or 21 mm and 40 or 43 ml/min for columns of internal diameter 30 mm. The trigger for the collection of the target species was the presence of the target m/z ratio value in the TIC MS signal. The gradient timetable was customised on the Rt behaviour of the target species.

Purification may also be performed using Biotage® Isolera or Biotage® SP1 flash chromatography systems, these instruments work with Biotage® KP-SIL cartridges, Biotage® KP-NH cartidges or Biotage® KP-C18 cartridges.

Unless otherwise stated, all reactions are typically performed under inert atmosphere (for example under Nitrogen).

The following abbreviations are used in the text: EtOAc, AcOEt, EA=ethyl acetate; Et$_2$O=diethyl ether; MeOH=methanol; THF=tetrahydrofuran; Tlc refers to thin layer chromatography on silica plates, and dried refers to a solution dried over anhydrous sodium sulphate; r.t. (RT) refers to room temperature; DMSO=dimethyl sulfoxide; DMF=N,N'-dimethylformamide; DCM=dichloromethane; EtOH=ethanol; DCE=dichloroethane; Cy, cHex=cyclohexane; TEA=trimethylamine; DIPEA=N,N-Diisopropylethylamine; AcOH=acetic acid; LAH=Lithium aluminum hydride; T3P=Propylphosphonic anhydride; SCX Cartridge=Strong Cation Exchange Cartridge; ipa=isopropylamine; FA=formic acid; HMTA=Hexamethylenetetramine.

Preparation 1: 4-methyl-1,3-oxazole-5-carboxylic acid

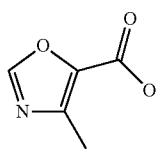

A stirred mixture of ethyl 2-chloro-3-oxobutanoate (16.8 mL, 121.51 mmol) and formamide (13.5 mL, 340.23 mmol) was heated to 120° C. After 6 hrs the mixture was allowed to cool to RT and stirred under nitrogen O/N. The mixture was treated with 3 M NaOH (120 mL, reaction moderately exothermic) and stirred at RT for 4 hrs. EtOAc (120 mL) was added and the phases allowed separating. The organic layer was discarded while the aqueous was acidified with 37% aqueous HCl to pH 2 (~40 mL). A precipitate started to form. The suspension was treated with EtOAc (160 mL) and, vigorously shaken. Phases were separated and the aqueous one was further extracted with EtOAc twice (120 mL). The combined organic layers were concentrated to low volume. Fresh EtOAc (160 mL) was added and the mixture evaporated to dryness under vacuum. The collected solid was placed in the oven at 45° C. O/N under reduced pressure to give 8.52 g of title compound (p1, y=44%), rusty brown solid. MS (m/z): 128.0 [MH]$^+$.

Preparation 2: 4-(1,3-oxazol-2-yl)benzoic acid

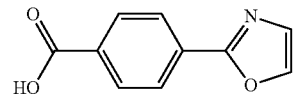

A solution of 4-carbamoylbenzoic (4.8 g, 29 mmol) and 2-bromo-1,1-diethoxyethane (8.7 mL, 58 mmol) in Dioxane (60 mL) was stirred at reflux (101° C.) for 3.5 hrs. The solids were filtered out and the filtrate was concentrated in vacuo. The residue was purified by reverse phase chromatography on C18 cartridge (eluent: Water+0.1% HCOOH to 30% ACN+0.1% HCOOH) to obtain 4-(1,3-oxazol-2-yl)benzoic acid (p2, 232 mg, y=4%). MS (m/z): 190.1 [MH]$^+$.

Preparation 3: 4-methyl-5-(4-methyl-1,3-oxazol-5-yl)-4H-1,2,4-triazole-3-thiol

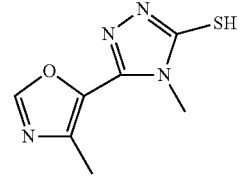

To a solution of 4-methyl-1,3-oxazole-5-carboxylic acid (p1, 2 g, 15.7 mmol) in DMF (9 mL), 4-Methyl-3-thiosemicarbazide (1.82 g, 17.27 mmol) was added. DIPEA (4.8 mL, 28.26 mmol) was added drop wise at RT, then the mixture was cooled in an ice bath before adding T3P (50% w/w in EtOAc) (14 mL, 23.55 mmol). The reaction was stirred at RT O/N. NaOH 4 M solution (15 mL) was added (resulting pH=8). The reaction was diluted with EtOAc and the two resulting phases were separated (the upper organic layer eliminated). The pH was increased to 11 NaOH 4 M and the mixture heated to 70° C. for 30-40 min. The clear rusty red solution was then cooled to RT for 3 hrs, then 37% HCl was slowly added till pH 5. The clear solution was extracted 3 times with DCM; combined organics were dried over a phase separator and concentrated to obtain a brown solid. It was purified by C18 cartridge (eluting from H$_2$O+0.1% HCOOH to 20% CH$_3$CN+0.1% HCOOH). Fractions containing the product were concentrated to reduce the volume, then extracted twice with DCM to obtain 605 mg of title compound (p3, y=17%) as yellow solid. MS (m/z): 197.1 [MH]$^+$.

Preparation 4: 4-(4-methyl-5-sulfanyl-4H-1,2,4-triazol-3-yl)benzamide

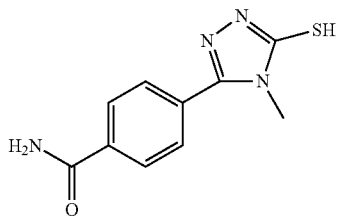 [SMILES: Cn1c(S)nnc1-c1ccc(C(N)=O)cc1]

To a stirred solution of 4-carbamoylbenzoic acid (0.5 g, 3 mmol) in DMF (1.5 mL), 4-methyl-3-thiosemicarbazide (0.350 g, 3.33 mmol) and DIPEA (2.68 mL, 4.5 mmol) were subsequently added. The mixture was cooled to 0° C. then T3P (50% wt/EA) (2.68 mL, 4.5 mmol) was added drop wise. The ice-bath was removed and the resulting reaction mixture was stirred at RT for 3 hrs. Aqueous 4M NaOH solution was added (resulting pH~8) followed by AcOEt and the two resulting phases were separated (the upper organic layer was eliminated). Additional 4M NaOH was added up to pH 11 then the mixture was heated to 70° C. and stirred for 40 min. The solution was cooled to RT and 6N HCl was slowly added until pH 5. The precipitate was filtered and washed with water and Cy. The collected solid was then dried under high vacuum affording 4-(4-methyl-5-sulfanyl-4H-1,2,4-triazol-3-yl)benzamide (p4, 545 mg, y=77%). MS (m/z): 235.1 [MH]$^+$.

The following intermediates listed in Table 1 were prepared in analogy with Preparation 4 starting from the listed carboxylic acids.

TABLE 1

| Prep num. | Structure | Name | Starting Material | Yield % | MS (m/z) |
|---|---|---|---|---|---|
| p5 | 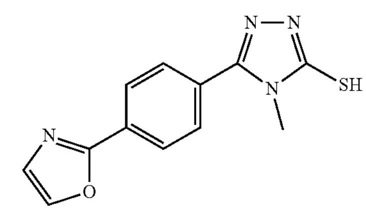 [SMILES: Cn1c(S)nnc1-c1ccc(-c2ncco2)cc1] | 4-methyl-5-[4-(1,3-oxazol-2-yl)phenyl]-4H-1,2,4-triazole-3-thiol | P2 | 35 | 258.9 |
| p6 | 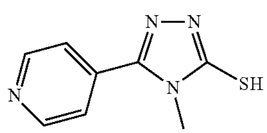 | 4-methyl-5-(pyridin-4-yl)-4H-1,2,4-triazole-3-thiol | | 84 | 193.1 |
| p7 | 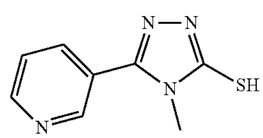 | 4-methyl-5-(pyridin-3-yl)-4H-1,2,4-triazole-3-thiol | | 61 | 193.1 |
| p8 | 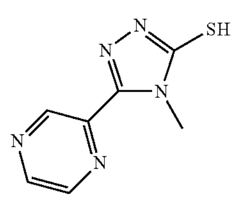 | 4-methyl-5-(pyrazin-2-yl)-4H-1,2,4-triazole-3-thiol | | 92 | 194.1 |
| p9 | 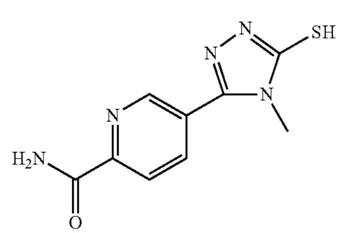 [SMILES: Cn1c(S)nnc1-c1ccc(C(N)=O)nc1] | 5-(4-methyl-5-sulfanyl-4H-1,2,4-triazol-3-yl)pyridine-2-carboxamide | | 74 | 236.1 |

TABLE 1-continued

| Prep num. | Structure | Name | Starting Material | Yield % | MS (m/z) |
|---|---|---|---|---|---|
| p10 | 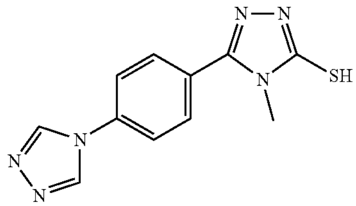 [SMILES: Cn1c(S)nnc1-c1ccc(-n2cnnc2)cc1] | 4-methyl-5-[4-(4H-1,2,4-triazol-4-yl)phenyl]-4H-1,2,4-triazole-3-thiol | | 55 | 259.2 |
| p11 | 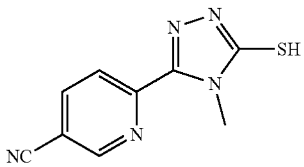 | 6-(4-methyl-5-sulfanyl-4H-1,2,4-triazol-3-yl)pyridine-3-carbonitrile | | 96 | 218.1 |
| p12 | 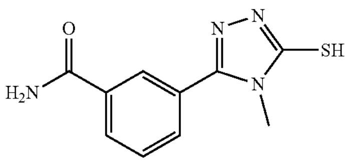 [SMILES: Cn1c(S)nnc1-c1cccc(C(N)=O)c1] | 3-(4-methyl-5-sulfanyl-4H-1,2,4-triazol-3-yl)-benzamide | | 71 | 235.2 |
| p13 | 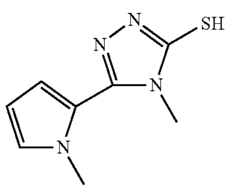 | 4-methyl-5-(1-methyl-1H-pyrrol-2-yl)-4H-1,2,4-triazole-3-thiol | | 8 | 195.0 |
| p14 | 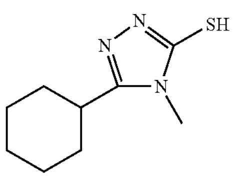 | 5-cyclohexyl-4-methyl-4H-1,2,4-triazole-3-thiol | | 70 | 198.0 |
| p15 | 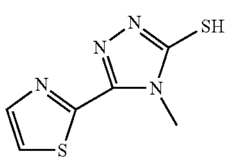 | 4-methyl-5-(1,3-thiazol-2-yl)-4H-1,2,4-triazole-3-thiol | | 59 | 198.9 |
| p16 | 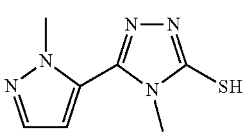 | 4-methyl-5-(1-methyl-1H-pyrazol-5-yl)-4H-1,2,4-triazole-3-thiol | | 64 | 196.1 |
| p17 | 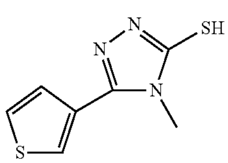 | 4-methyl-5-(thiophen-3-yl)-4H-1,2,4-triazole-3-thiol | | 43 | 197.9 |

TABLE 1-continued

| Prep num. | Structure | Name | Starting Material | Yield % | MS (m/z) |
|---|---|---|---|---|---|
| p18 | 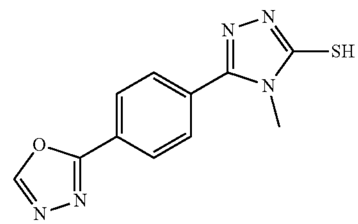 [SMILES: Cn1c(S)nnc1-c1ccc(-c2nnco2)cc1] | 4-methyl-5-[4-(1,3,4-oxadiazol-2-yl)phenyl]-4H-1,2,4-triazole-3-thiol | | 55 | 260.1 |
| p19 | 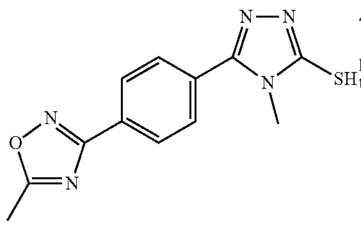 | 4-methyl-5-[4-(5-methyl-1,2,4-oxadiazol-3-yl)-phenyl]-4H-1,2,4-triazole-3-thiol | | 44 | 274.2 |
| p20 | 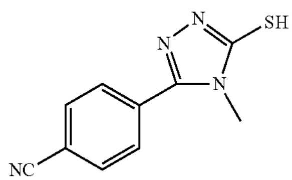 | 4-(4-methyl-5-sulfanyl-4H-1,2,4-triazol-3-yl)-benzonitrile | | Quant. | 217.1 |
| p21 | 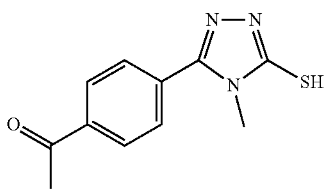 [SMILES: CC(=O)c1ccc(-c2nnc(S)n2C)cc1] | 1-[4-(4-methyl-5-sulfanyl-4H-1,2,4-triazol-3-yl)-phenyl]ethan-1-one | | 17 | 234.2 |
| p22 | 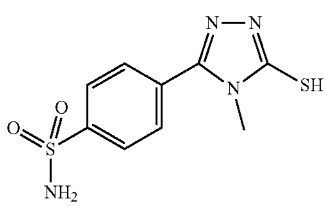 [SMILES: Cn1c(S)nnc1-c1ccc(S(N)(=O)=O)cc1] | 4-(4-methyl-5-sulfanyl-4H-1,2,4-triazol-3-yl)benzene-1-sulfonamide | | 37 | 271.1 |

Preparation 23: 6-(4-methyl-5-sulfanyl-4H-1,2,4-triazol-3-yl)pyridine-3-carboxamide

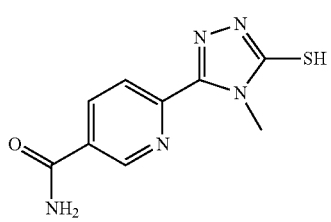 [SMILES: Cn1c(S)nnc1-c1ccc(C(N)=O)cn1]

A mixture of 6-(4-methyl-5-sulfanyl-4H-1,2,4-triazol-3-yl)pyridine-3-carbonitrile (p11, 1.47 g, 6.75 mmol) and crushed KOH (1.14 g, 20.25 mmol) in t-BuOH (90 mL) was heated to 90° C. and stirred for 1.5 h. After allowing the mixture to reach RT it was filtered and the yellow solid washed with t-BuOH then dried under vacuum. The solid was taken up with water, the pH was brought to 4-5 by adding 37% HCl then the mixture was filtered, the solid was washed with water and dried under vacuum at 45° C. O/N affording 6-(4-methyl-5-sulfanyl-4H-1,2,4-triazol-3-yl)pyridine-3-carboxamide (p23, 1.39 g, y=88%). MS (m/z): 236.1 [MH]$^+$.

Preparation 24: (4-chlorobutyl)sulfanyl]-4-methyl-5-(4-methyl-1,3-oxazol-5-yl)-4H-1,2,4-triazole

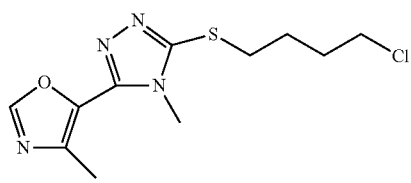 [SMILES: Cc1ncoc1-c1nnc(SCCCCCl)n1C]

To a suspension of 4-methyl-5-(4-methyl-1,3-oxazol-5-yl)-4H-1,2,4-triazole-3-thiol (p3, 300 mg, 1.53 mmol) in a mixture MeOH/Acetone (0.75 mL/1.6 mL) at RT, 1-Bromo-4-chlorobutane (230 μL, 1.99 mmol) was added followed by K₂CO₃ (296 mg, 2.14 mmol) and the mixture was stirred at RT 4 hrs. Then it was partitioned between water and EtOAc and phases were separated. Organic one was washed with brine then dried and concentrated under reduced pressure. Crude material was purified by FC on silica gel (eluting from cHex to EtOAc) affording (4-chlorobutyl)sulfanyl]-4-methyl-5-(4-methyl-1,3-oxazol-5-yl)-4H-1,2,4-triazole (p24, 270 mg, y=61%). MS (m/z): 287.1 [MH]⁺.

Preparation 25: 3-[(3-chloropropyl)sulfanyl]-4-methyl-5-(4-methyl-1,3-oxazol-5-yl)-4H-1,2,4-triazole

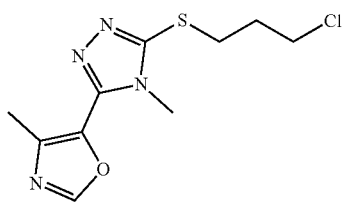 [SMILES: Cc1ncoc1-c1nnc(SCCCCl)n1C]

To a suspension of 4-methyl-5-(4-methyl-1,3-oxazol-5-yl)-4H-1,2,4-triazole-3-thiol (p3, 400 mg, 2.03 mmol) in a mixture MeOH/Acetone (1.3 mL/3.2 mL) at RT, 1-Bromo-3-chloropropane (260 μL, 2.64 mmol) was added, followed by K₂CO₃ (392 mg, 2.84 mmol) and the mixture was stirred at RT for 4.5 hrs. It was partitioned between water and EtOAc and phases were separated. Organic one was washed with brine then dried and concentrated under reduced pressure to obtain 509 mg of yellow solid. It was purified by FC on SiO₂ cartridge (eluting from cHex to EtOAc) affording 3-[(3-chloropropyl)sulfanyl]-4-methyl-5-(4-methyl-1,3-oxazol-5-yl)-4H-1,2,4-triazole (p25, 400 mg, y=65%), as pale yellow solid. MS (m/z): 273.1 [MH]⁺.

The following intermediates listed in Table 2 were sinthesised in analogy with Preparation 25 reacting the corresponding thiotriazole with 1-bromo,3-chloropropane.

TABLE 2

| Prep num. | Structure | Name | Starting Material | Yield % | MS (m/z) |
|---|---|---|---|---|---|
| p26 | 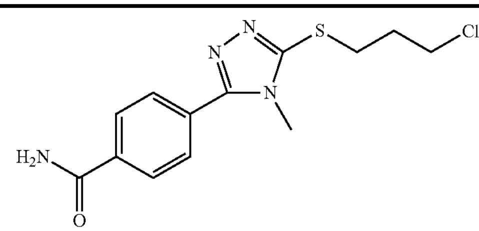 | 4-{5-[(3-chloropropyl)-sulfanyl]-4-methyl-4H-1,2,4-triazol-3-yl}benzamide | p7 | 55 | 311.1 |
| p27 | 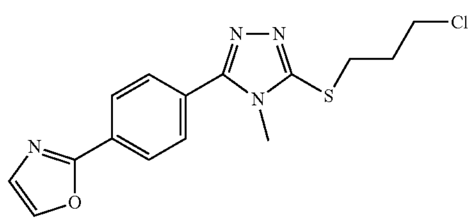 [SMILES: Cn1c(SCCCCl)nnc1-c1ccc(-c2ncco2)cc1] | 3-[(3-chloropropyl)sulfanyl]-4-methyl-5-[4-(1,3-oxazol-2-yl)phenyl]-4H-1,2,4-triazole | p9 | 61 | 335.2 |
| p28 | 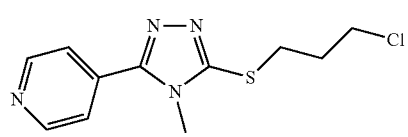 [SMILES: Cn1c(SCCCCl)nnc1-c1ccncc1] | 4-{5-[(3-chloropropyl)-sulfanyl]-4-methyl-4H-1,2,4-triazol-3-yl}pyridine | p4 | 83 | 269.2 |
| p29 | 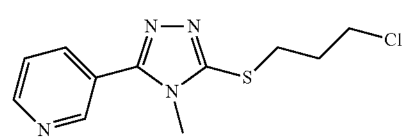 [SMILES: Cn1c(SCCCCl)nnc1-c1cccnc1] | 3-{5-[(3-chloropropyl)-sulfanyl]-4-methyl-4H-1,2,4-triazol-3-yl}pyridine | p5 | 88 | 269.2 |
| p30 | 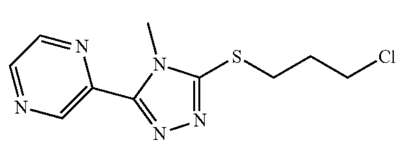 [SMILES: Cn1c(SCCCCl)nnc1-c1cnccn1] | 2-{5-[(3-chloropropyl)-sulfanyl]-4-methyl-4H-1,2,4-triazol-3-yl}pyrazine | p6 | 84 | 270.1 |

TABLE 2-continued

| Prep num. | Structure | Name | Starting Material | Yield % | MS (m/z) |
|---|---|---|---|---|---|
| p31 | 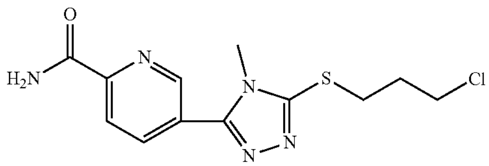 [SMILES: Cn1c(SCCCCl)nnc1-c1ccc(C(N)=O)nc1] | 5-{5-[(3-chloropropyl)-sulfanyl]-4-methyl-4H-1,2,4-triazol-3-yl}pyridine-2-carboxamide | p8 | 31 | 312.2 |
| p32 | 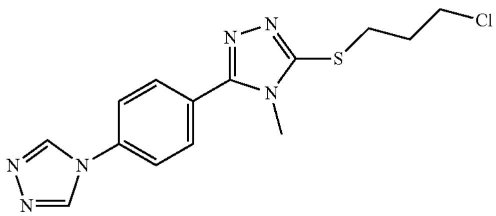 [SMILES: Cn1c(SCCCCl)nnc1-c1ccc(-n2cnnc2)cc1] | 3-[(3-chloropropyl)sulfanyl]-4-methyl-5-[4-(4H-1,2,4-triazol-4-yl)phenyl]-4H-1,2,4-triazole | p10 | 49 | 335.2 |
| p33 | 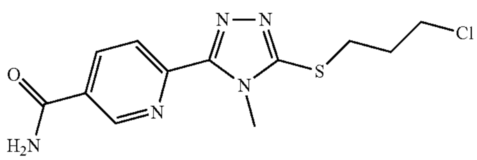 [SMILES: Cn1c(SCCCCl)nnc1-c1ccc(C(N)=O)cn1] | 6-{5-[(3-chloropropyl)-sulfanyl]-4-methyl-4H-1,2,4-triazol-3-yl}pyridine-3-carboxamide | p23 | 79 | 312.1 |
| p34 | 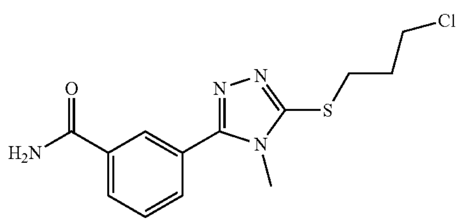 [SMILES: Cn1c(SCCCCl)nnc1-c1cccc(C(N)=O)c1] | 3-{5-[(3-chloropropyl)-sulfanyl]-4-methyl-4H-1,2,4-triazol-3-yl}benzamide | p11 | 48 | 311.2 |
| p35 | 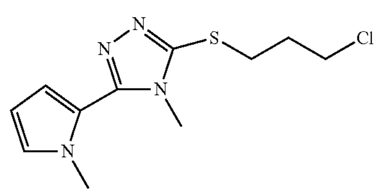 [SMILES: Cn1cccc1-c1nnc(SCCCCl)n1C] | 3-[(3-chloropropyl)sulfanyl]-4-methyl-5-(1-methyl-1H-pyrrol-2-yl)-4H-1,2,4-triazole | p17 | 76 | 271.0 |
| p36 | 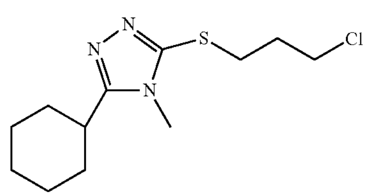 [SMILES: Cn1c(SCCCCl)nnc1C1CCCCC1] | 3-[(3-chloropropyl)sulfanyl]-5-cyclohexyl-4-methyl-4H-1,2,4-triazole | p21 | 88 | 274.0 |
| p37 | 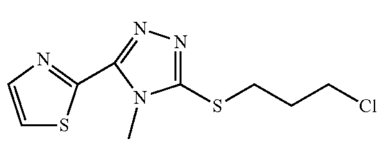 [SMILES: Cn1c(SCCCCl)nnc1-c1nccs1] | 3-[(3-chloropropyl)sulfanyl]-4-methyl-5-(1,3-thiazol-2-yl)-4H-1,2,4-triazole | p19 | 84 | 274.9 |
| p38 | 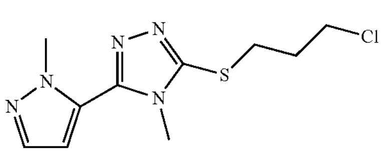 [SMILES: Cn1nccc1-c1nnc(SCCCCl)n1C] | 3-[(3-chloropropyl)sulfanyl]-4-methyl-5-(1-methyl-1H-pyrazol-5-yl)-4H-1,2,4-triazole | p18 | 87 | 272.3 |

TABLE 2-continued

| Prep num. | Structure | Name | Starting Material | Yield % | MS (m/z) |
|---|---|---|---|---|---|
| p39 | 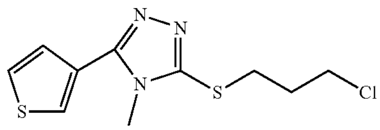 [SMILES: Cn1c(SCCCCl)nnc1-c1ccsc1] | 3-[(3-chloropropyl)sulfanyl]-4-methyl-5-(thiophen-3-yl)-4H-1,2,4-triazole | p20 | 77 | 273.9 |
| p40 | 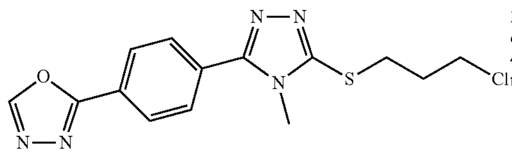 [SMILES: Cn1c(SCCCCl)nnc1-c1ccc(-c2nnco2)cc1] | 2-(4-{5-[(3-chloropropyl)sulfanyl]-4-methyl-4H-1,2,4-triazol-3-yl}phenyl)-1,3,4-oxadiazole | p16 | Quant | 336.2 |
| p41 | 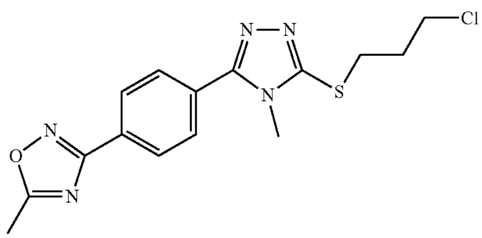 [SMILES: Cc1nc(-c2ccc(-c3nnc(SCCCCl)n3C)cc2)no1] | 3-(4-{5-[(3-chloropropyl)sulfanyl]-4-methyl-4H-1,2,4-triazol-3-yl}phenyl)-5-methyl-1,2,4-oxadiazole | p15 | 53 | 350.2 |
| p42 | 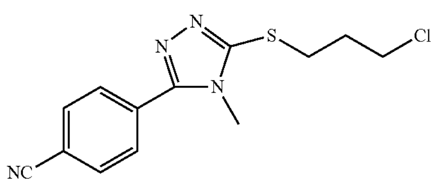 [SMILES: Cn1c(SCCCCl)nnc1-c1ccc(C#N)cc1] | 4-{5-[(3-chloropropyl)sulfanyl]-4-methyl-4H-1,2,4-triazol-3-yl}benzonitrile | p14 | 93 | 293.2 |
| p43 | 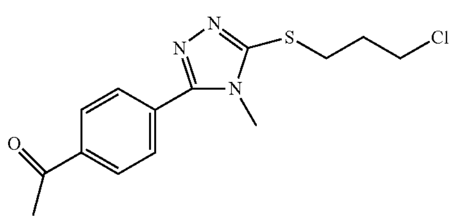 [SMILES: CC(=O)c1ccc(-c2nnc(SCCCCl)n2C)cc1] | 1-(4-{5-[(3-chloropropyl)sulfanyl]-4-methyl-4H-1,2,4-triazol-3-yl}phenyl)ethan-1-one | p12 | 59 | 309.9 |
| p44 | 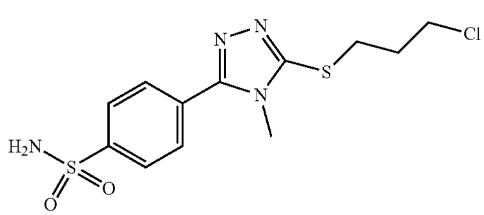 [SMILES: Cn1c(SCCCCl)nnc1-c1ccc(S(N)(=O)=O)cc1] | 4-{5-[(3-chloropropyl)sulfanyl]-4-methyl-4H-1,2,4-triazol-3-yl}benzene-1-sulfonamide | p13 | 48 | 347.1 |

Preparation 45:
2-amino-1-(4-fluorophenyl)ethan-1-one hydrochloride

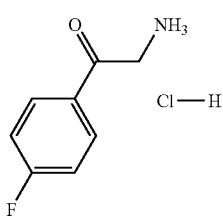

2-Bromo-4'-fluoroacetophenone (1.5 g, 6.9 mmol) was added to a solution of HMTA (1.06 g, 7.59 mmol) in CHCl$_3$ (25 mL). The mixture was stirred at RT for 16 hrs. The precipitate was filtered and the cake was suspended in EtOH (30 mL) and diluted with 37% HCl (4.2 mL), then stirred at RT for 12 hrs. The precipitate was filtered, the filtrate was concentrated in vacuum to provide an off-white solid that was triturated with isopropanol to afford 2-amino-1-(4-fluorophenyl)ethan-1-one hydrochloride (p45, 1 g, y=76%) as white solid that was used as such in the next step. MS (m/z): 154.2 [MH]$^+$.

Preparation 46: 2-amino-1-(4-fluorophenyl)ethan-1-ol

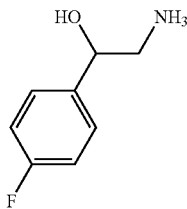

To a solution of 2-amino-1-(4-fluorophenyl)ethan-1-one hydrochloride (p45, 1 g, 5.27 mmol) in 30 mL of MeOH, stirred at 0° C. under $N_2$, $NaBH_4$ (380 mg, 10 mmol) was added. The solution was stirred at 0° C. for 30 min. Water was added until gas evolution ceased. Solvent was removed in vacuo, the residue was charged on a SCX cartridge washing with MeOH and eluting with 1M $NH_3$ in MeOH to afford 2-amino-1-(4-fluorophenyl)ethan-1-ol (p46, 1 g) as orange oil, that was used as crude in the next step. NMR: $^1H$ NMR (DMSO-d6) δ: 7.31-7.41 (m, 2H), 7.13 (m, 2H), 5.21-5.37 (br. s, 1H), 4.41-4.50 (m, 1H), 2.54-2.69 (m, 2H), 1.31-1.89 (br. s, 2H)

Preparation 47: 2-chloro-N-[2-(4-fluorophenyl)-2-hydroxyethyl]acetamide

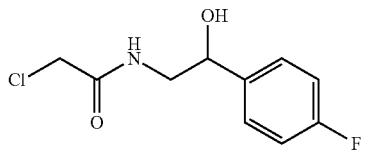 [SMILES: O=C(CCl)NCC(O)c1ccc(F)cc1]

To a solution of 2-amino-1-(4-fluorophenyl)ethan-1-ol (p46, 800 mg, 5.15 mmol) in 30 mL of DCM, stirred at 0° C. under $N_2$, TEA (2.15 mL, 15.450 mmol) was added, followed by drop wise addition of chloro acetyl chloride (0.41 mL, 5.15 mmol). The solution was stirred at 0° C. for 1 h. $NH_4Cl$ saturated solution was added and the product was extracted several times with DCM. The organic phase was washed with brine, dried and evaporated. The residue was purified by FC on silica column (eluting from cHex to 60% of EtOAc) to afford 2-chloro-N-[2-(4-fluorophenyl)-2-hydroxyethyl]acetamide (p47, 580 mg, y=49%) as pale yellow solid. MS (m/z): 232.1 $[MH]^+$.

Preparation 48: 6-(4-fluorophenyl)morpholin-3-one

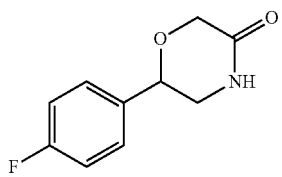 [SMILES: O=C1COC(c2ccc(F)cc2)CN1]

To a stirred solution of 2-chloro-N-[2-(4-fluorophenyl)-2-hydroxyethyl]acetamide (p47, 580 mg, 2.51 mmol) in THF (35 mL), at 0° C., t-BuOK (583 mg, 5.2 mmol) was added portion-wise and the resulting reaction mixture was left stirring at RT for 1 h. The reaction mixture was neutralized with $NH_4Cl$ and extracted with EtOAc several times. The organic phase was washed with brine, dried and evaporated. The resulting yellow solid was triturated with $Et_2O$ affording 6-(4-fluorophenyl)morpholin-3-one (p48, 560 mg, y=crude) as white solid. MS (m/z): 196.1 $[MH]^+$.

Preparation 49: 2-(4-fluorophenyl)morpholine

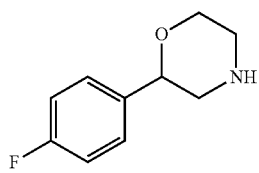

To a stirred solution of 6-(4-fluorophenyl)morpholin-3-one (p48, 560 mg, 2.51 mmol) in THF (20 mL), $LiAlH_4$ 1 M in THF (3.76 mL, 3.76 mmol) was added drop wise, the resulting solution was then heated at reflux for 1 h. It was cooled at 0° C. and quenched with $Na_2SO_4$ $10*H_2O$ until gas evolution ceased. The suspension was filtered and the salts were washed with EtOAc. After evaporation of the organic solvent 2-(4-fluorophenyl)morpholine was obtained as yellow oil (p49, 130 mg, y=29%). MS (m/z): 182.1 $[MH]^+$.

Preparation 50: 2-amino-1-[4-(trifluoromethyl)phenyl]ethan-1-one hydrochloride

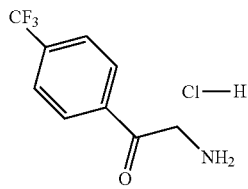

2-bromo-1-[4-(trifluoromethyl)phenyl]ethan-1-one (2.7 g, 10.11 mmol) was dissolved in acetonitrile (45 mL), then Sodium diformylamide (1.105 g, 11.62 mmol) was added one pot. The mixture was stirred ar RT for 2 hrs, then at 70° C. for 2 hrs. The solvent was removed and EtOH (35 mL) was added, followed by conc. HCl 37% (5.9 mL) and the reaction was stirred at reflux for 1.5 hr. The precipitate was filtered and dried to give 2-amino-1-[4-(trifluoromethyl)phenyl]ethan-1-one hydrochloride (p50, 2.3 g, y=95%) as white solid. MS (m/z): 204.1 $[MH]^+$.

Preparation 51: 2-amino-1-[4-(trifluoromethyl)phenyl]ethan-1-ol

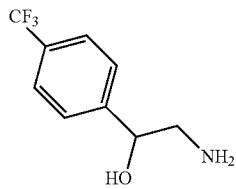 [SMILES: NCC(O)c1ccc(C(F)(F)F)cc1]

To a solution of 2-amino-1-[4-(trifluoromethyl)phenyl] ethan-1-one hydrochloride (p50, 2.3 g, 9.6 mmol) in MeOH (40 mL), stirred at 0° C. under N₂, NaBH₄ (545 mg, 14.4 mmol) was added. The solution was stirred at 0° C. for 30 min. H₂O was added until gas evolution ceased. Solvent was removed in vacuo, the residue was charged on a SCX cartridge washing with MeOH and eluting with 1N NH₃ in MeOH affording after evaporation 2-amino-1-[4-(trifluoromethyl)-phenyl]ethan-1-ol (p51, 1.26 g, y=64%) as pale yellow wax. MS (m/z): 206.1 [MH]⁺.

Preparation 52: 2-chloro-N-{2-hydroxy-2-[4-(trifluoromethyl)phenyl]ethyl}acetamide

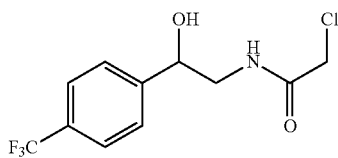 [SMILES: O=C(CCl)NCC(O)c1ccc(C(F)(F)F)cc1]

To a solution of 2-amino-1-[4-(trifluoromethyl)phenyl]ethan-1-ol (p51, 1.26 g, 6.14 mmol) in DCM (15 mL) a solution of NaOH (590 mg, 14.73 mmol) in water (10 mL) was added, then the mixture was brought to 0° C. and 2-chloroacetyl chloride (0.54 mL, 6.75 mmol) was added over 5 min under vigorous magnetic stirring. The ice-bath was removed and the reaction mixture was stirred at RT 2.5 hrs. The reaction mixture was diluted with DCM, the organic phase was washed with water and brine, dried over sodium sulfate and the solvent removed under vacuum to give 2-chloro-N-{2-hydroxy-2-[4-(trifluoromethyl)phenyl]ethyl}acetamide (p52, 1.66 g, y=96%) as white solid. MS (m/z): 282.2 [MH]⁺.

Preparation 53: 6-[4-(trifluoromethyl)phenyl]morpholin-3-one

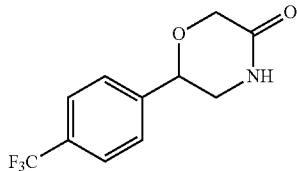

To a stirred clear yellow solution of 2-chloro-N-{2-hydroxy-2-[4-(trifluoromethyl)-phenyl]ethyl}acetamide (p52, 1.66 g, 5.89 mmol) in THF (50 mL), at 0° C., t-BuOK (1.32 g, 11.78 mmol) was added portion-wise and the resulting reaction mixture was left stirring at RT for 45'. The reaction mixture was neutralized with NH₄Cl sat. sol. and extracted with EtOAc 3 times. The organic phase was washed with brine, dried and evaporate to obtain 6-[4-(trifluoromethyl)phenyl]-morpholin-3-one (p53, 1.45 g) as yellow wax that was used as crude in the next step. MS (m/z): 282.2 [MH]⁺.

Preparation 54: 2-[4-(trifluoromethyl)phenyl]morpholine

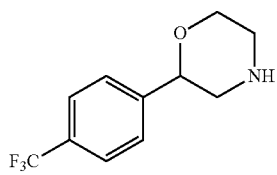 [SMILES: FC(F)(F)c1ccc(C2CNCCO2)cc1]

To a stirred solution of 6-[4-(trifluoromethyl)phenyl]morpholin-3-one (p53, 1.45 g, 5.89 mmol) in THF (40 mL), LiAlH₄ 1M in THF (8.83 mL, 8.83 mmol) was added dropwise at 0° C., the resulting solution was then heated at reflux for 1 h. It was cooled again to 0° C. and quenched with Na₂SO₄*10 H₂O until gas evolution ceased. The suspension was filtered, the salts were washed with EtOAc and the solvent was evaporated to obtain 2-[4-(trifluoromethyl)phenyl]morpholine (p54, 1.18 g, y=86%) as yellow oil that was used as such. MS (m/z): 232.2 [MH]⁺.

Preparation 55: 2-amino-1-[2-fluoro-4-(trifluoromethyl)phenyl]ethan-1-one hydrochloride

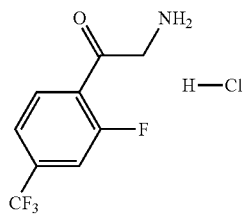

2-fluoro-4-(trifluoromethyl)phenacyl bromide (4 g, 14 mmol) was added to a solution of HMTA (2.16 g, 3.85 mmol) in CCl₄ (30 mL). The mixture was stirred at RT for 16 hrs. The solvent was evaporated and the residue triturated with Et₂O. The solid was suspended in EtOH (60 mL) and diluted with 37% HCl (8.5 mL), then stirred at RT for 36 hrs. The precipitate was filtered and the filtrate was concentrated in vacuo to provide a yellow solid that was triturated with Et₂O affording 2-amino-1-[2-fluoro-4-(trifluoromethyl)phenyl]ethan-1-one hydrochloride (p55, 3.6 g, y=quant) as pale yellow solid. MS (m/z): 222.1 [MH]⁺.

Preparation 56: 2-amino-1-[2-fluoro-4-(trifluoromethyl)phenyl]ethan-1-ol

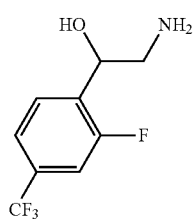 [SMILES: NCC(O)c1ccc(C(F)(F)F)cc1F]

To a solution of 2-amino-1-[2-fluoro-4-(trifluoromethyl)phenyl]ethan-1-one hydrochloride (p55, 1 g, 3.88 mmol) in 30 mL of MeOH, stirred at 0° C. under N₂, NaBH₄ (330 mg, 4.27 mmol) was added. The solution was stirred at 0° C. for 30 min and then H₂O was added until gas evolution ceased. Solvent was removed in vacuo and the residue was loaded on a SCX cartridge eluting with 1M NH₃ in MeOH to afford, after evaporation, 2-amino-1-[2-fluoro-4-(trifluoromethyl) phenyl]-ethan-1-ol (p56, 0.75 g, y=86%) as pale yellow oil. MS (m/z): 224.2 [MH]⁺.

Preparation 57: 2-chloro-N-{2-[2-fluoro-4-(trifluoromethyl)phenyl]-2-oxoethyl}acetamide

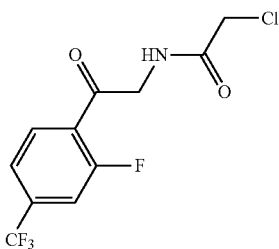 [SMILES: O=C(CCl)NCC(=O)c1ccc(C(F)(F)F)cc1F]

To a solution of 2-amino-1-[2-fluoro-4-(trifluoromethyl) phenyl]ethan-1-ol (p56, 750 mg, 3.36 mmol) in 8 mL of DCM and 4 mL of 1 M NaOH, stirred at 0° C. under N₂, 2-chloro-acetyl chloride (0.3 mL, 3.7 mmol) was added drop-wise. The solution was stirred at RT for 1 h. The product was extracted several times with DCM. The organic phase was washed with brine, dried and evaporated to afford 2-chloro-N-({2-[2-fluoro-4-(trifluoromethyl)phenyl]-2-oxoethyl}acetamide (p57, 850 mg, y=84%) as pale yellow solid that was used as such in the next step. MS (m/z): 300.2 [MH]⁺.

Preparation 58: 6-[2-fluoro-4-(trifluoromethyl)phenyl]morpholin-3-one

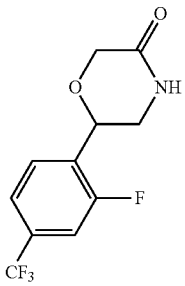 [SMILES: O=C1COC(c2ccc(C(F)(F)F)cc2F)CN1]

To a stirred solution of 2-chloro-N-{2-[2-fluoro-4-(trifluoromethyl)phenyl]-2-oxoethyl}acetamide (p57, 850 mg, 2.83 mmol) in THF (30 mL), at 0° C., t-BuOK (635 mg, 5.66 mmol) was added portion-wise and the resulting reaction mixture was left stirring at RT for 1 h. The reaction mixture was neutralized with NH₄Cl ss and extracted with EtOAc several times. The organic phase was washed with brine, dried and evaporated. Crude material was purified by FC on silica gel (eluting from cHex to EtOAc) to afford 6-[2-fluoro-4-(trifluoromethyl)phenyl]morpholin-3-one (p58, 340 mg, y=45%). as pale yellow solid. MS (m/z): 264.2 [MH]⁺.

Preparation 59: 2-[2-fluoro-4-(trifluoromethyl)phenyl]morpholine

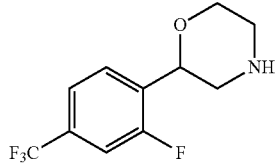

To a stirred solution of 6-[2-fluoro-4-(trifluoromethyl) phenyl]morpholin-3-one (p58, 340 mg, 1.29 mmol) in THF (10 mL), LiAlH₄ 1M in THF (1.93 mL, 1.93 mmol) was added drop wise and the resulting solution was then heated at reflux for 1 h. The mixture was cooled down to 0° C. and quenched with Na₂SO₄ 10*H₂O until gas evolution ceased. The suspension was filtered and the salts were washed with EtOAc. After evaporation of the organic solvent 2-[2-fluoro-4-(trifluoromethyl)phenyl]morpholine was afforded as yellow solid (p59, 300 mg, y=93%). MS (m/z): 250.2 [MH]⁺.

Example 1

2-(4-fluorophenyl)-4-(3-({[4-methyl-5-(4-methyl-1,3-oxazol-5-yl)-4H-1,2,4-triazol-3-yl]sulfanyl}propyl)morpholine (E1)

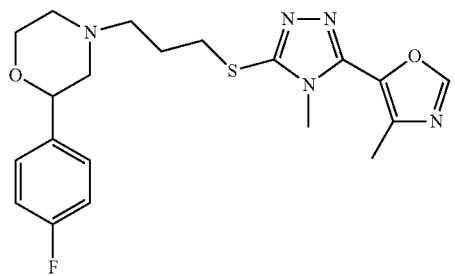 [SMILES: Cc1ncoc1-c1nnc(SCCCN2CCOC(c3ccc(F)cc3)C2)n1C]

2-(4-fluorophenyl)morpholine (p49, 50 mg, 0.276 mmol), 3-[(3-chloropropyl)sulfanyl]-4-methyl-5-(4-methyl-1,3-oxazol-5-yl)-4H-1,2,4-triazole (p25, 90 mg, 0.33 mmol), Na₂CO₃ (35 mg, 0.33 mmol) and NaI (50 mg, 0.33 mmol) were dissolved in DMF (0.2 mL) and heated at 60° C. O/N. The mixture was diluted with water and EtOAc and extracted several times with EtOAc. The organic phase was washed with brine, dried and evaporated. The residue was purified by FC on silica gel (eluting from DCM to 5% of MeOH) to afford 2-(4-fluorophenyl)-4-(3-{[4-methyl-5-(4-methyl-1,3-oxazol-5-yl)-4H-1,2,4-triazol-3-yl]sulfanyl}propyl)morpholine (E1, 62 mg, y=54%) as pale yellow wax. NMR: ¹H NMR (CDCl₃) δ: 7.94 (s, 1H), 7.32-7.41 (m, 2H), 6.99-7.10 (m, 2H), 4.51-4.57 (m, 1H), 4.01-4.06 (m, 1H), 3.78-3.86 (m, 1H), 3.72 (s, 3H), 3.33-3.44 (m, 2H), 2.92 (d, 1H), 2.80 (d, 1H), 2.49-2.61 (m, 5H), 2.23-2.30 (m, 1H), 1.99-2.13 (m, 3H). MS (m/z): 418.3 [MH]⁺.

Example 2 and 3

(2S or 2R)-2-(4-fluorophenyl)-4-(3-{[4-methyl-5-(4-methyl-1,3-oxazol-5-yl)-4H-1,2,4-triazol-3-yl]sulfanyl}propyl)morpholine (Example 2, Enantiomer 2S)

(2R or 2S)-2-(4-fluorophenyl)-4-(3-({[4-methyl-5-(4-methyl-1,3-oxazol-5-yl)-4H-1,2,4-triazol-3-yl]sulfanyl}propyl)morpholine (Example 3, Enantiomer 2S)

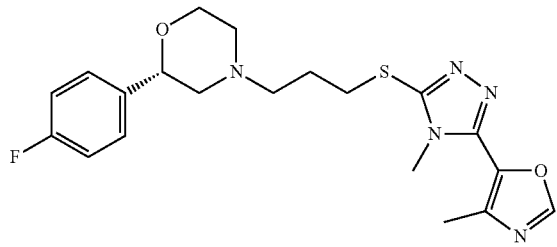

2-(4-fluorophenyl)-4-(3-({[4-methyl-5-(4-methyl-1,3-oxazol-5-yl)-4H-1,2,4-triazol-3-yl]sulfanyl}propyl)morpholine (E1, 60 mg) was separated into the single enantiomers by preparative chiral HPLC, obtaining 23.2 mg of (2S or 2R)-2-(4-fluorophenyl)-4-(3-{[4-methyl-5-(4-methyl-1,3-oxazol-5-yl)-4H-1,2,4-triazol-3-yl]sulfanyl}propyl)morpholine (E2, Enantiomer 1) and 23.2 mg of (2R or 2S)-2-(4-fluorophenyl)-4-(3-{[4-methyl-5-(4-methyl-1,3-oxazol-5-yl)-4H-1,2,4-triazol-3-yl]sulfanyl}propyl)morpholine (E3, Enantiomer 2)

Preparative Chromatography:

| | |
|---|---|
| Column | Chiralcel AD-H (25 × 2 cm), 5 μm |
| Mobile phase | n-Hexane/Ethanol 50/50 v/v |
| Flow rate (mL/min) | 14 |
| DAD detection | 220 nm |
| Loop | 1000 μL |
| injection | 15 mg (each injection) |

Example 2, Enantiomer 1: ret. time 14.3 min, 100% ee. MS (m/z): 418.3 [MH]$^+$. Example 3, Enantiomer 2: ret. time 16.3 min, 96.2% ee MS (m/z): 418.3 [MH]$^+$.

Example 4

4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine (E4)

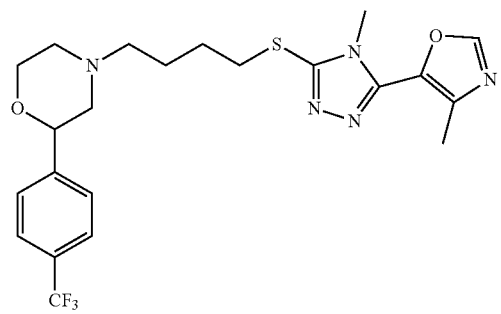

The title compound was prepared in analogy to the method described in Example 1 in 38 mg yield (E4, y=46%) from 2-[4-(trifluoromethyl)phenyl]morpholine (p54, 50 mg, 0.17 mmol) and 3-[(4-chlorobutyl)sulfanyl]-4-methyl-5-(4-methyl-1,3-oxazol-5-yl)-4H-1,2,4-triazole (p24, 60 mg, 0.21 mmol). NMR: $^1$H NMR (Acetone-d$_6$) δ: 8.27 (s, 1H), 7.68 (s, 4H), 4.59-4.66 (m, 1H), 3.96-4.05 (m, 1H), 3.79 (s, 3H), 3.72-3.79 (m, 1H), 3.29 (s, 2H), 3.01-3.10 (m, 1H), 2.80-2.85 (m, 1H), 2.43 (s, 5H), 2.12-2.22 (m, 1H), 1.80-1.97 (m, 3H), 1.65-1.77 (m, 2H). MS (m/z): 482.3 [MH]$^+$.

Example 5 and 6

(2S or 2R)-4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine (E5, Enantiomer 1)

(2R or 2S)-4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine (E6, Enantiomer 2)

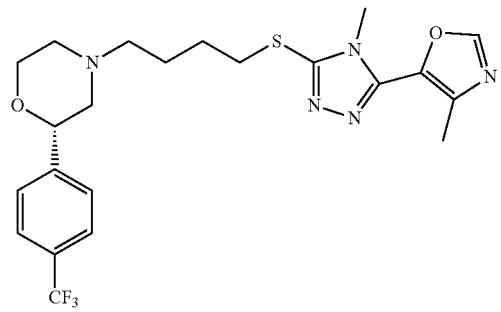 [SMILES: Cc1ncoc1-c1nnc(SCCCCN2CCOC(c3ccc(C(F)(F)F)cc3)C2)n1C]

-continued

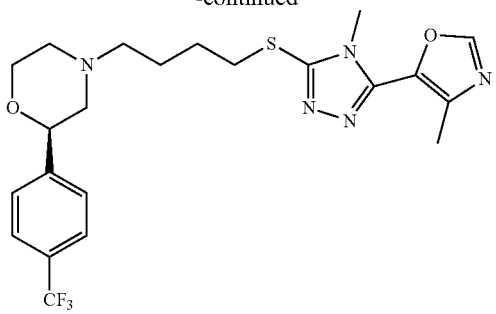

4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine (E4, 35 mg) was separated into the single enantiomers by preparative chiral HPLC, obtaining 9 mg of (2S or 2R)-4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine (E5, Enantiomer 1) and 8.5 mg of (2R or 2S)-4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine (E6, Enantiomer 2).

Preparative Chromatography:

| | |
|---|---|
| Column | Chiralcel AD-H (25 × 2 cm), 5 μm |
| Mobile phase | n-Hexane/(2-Propanol/Methanol 1/1 + 0.1% ipa) 60/40 v/v |
| Flow rate (mL/min) | 16 |
| DAD detection | 220 nm |
| Loop | 500 μL |
| injection | 6 mg (each injection) |

Example 5, Enantiomer 1: ret. time 8.4 min, 100% ee. MS (m/z): 482.3 [MH]⁺. Example 6, Enantiomer 2: ret. time 9.4 min, 92.4% ee. MS (m/z): 482.3 [MH]⁺.

Example 7

4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine (E7)

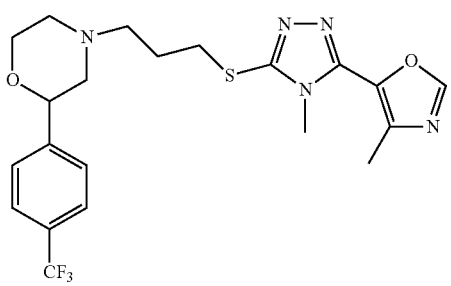 [SMILES: Cc1ncoc1-c1nnc(SCCCN2CCOC(c3ccc(C(F)(F)F)cc3)C2)n1C]

The title compound was prepared in analogy to the method described in Example 1 in 38 mg yield (E7, y=48%) from 2-[4-(trifluoromethyl)phenyl]morpholine (p54, 50 mg, 0.17 mmol) and 3-[(3-chloropropyl)sulfanyl]-4-methyl-5-(4-methyl-1,3-oxazol-5-yl)-4H-1,2,4-triazole (p25, 57 mg, 0.21 mmol). NMR: ¹H NMR (Acetone-d₆) δ: 8.27 (s, 1H), 7.60-7.75 (m, 4H), 4.61-4.68 (m, 1H), 3.99-4.06 (m, 1H), 3.73-3.85 (m, 4H), 3.37-3.49 (m, 1H), 3.24-3.35 (m, 1H), 3.09-3.17 (m, 1H), 2.78-2.86 (m, 2H), 2.47-2.61 (m, 2H), 2.44 (s, 3H), 2.16-2.26 (m, 1H), 1.96-2.07 (m, 3H). MS (m/z): 468.3 [MH]⁺.

Example 8 and 9

(2S or 2R)-4-(3-({[4-methyl-5-(4-methyl-1,3-oxazol-5-yl)-4H-1,2,4-triazol-3-yl]sulfanyl}propyl)-2-[4-(trifluoromethyl)phenyl]morpholine (E8, Enantiomer 1)

(2R or 2S)-4-(3-{[4-methyl-5-(4-methyl-1,3-oxazol-5-yl)-4H-1,2,4-triazol-3-yl]sulfanyl)}propyl)-2-[4-(trifluoromethyl)phenyl]morpholine (E9, Enantiomer 2)

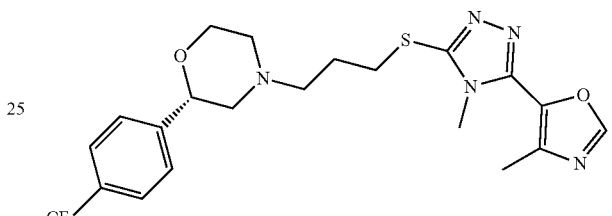

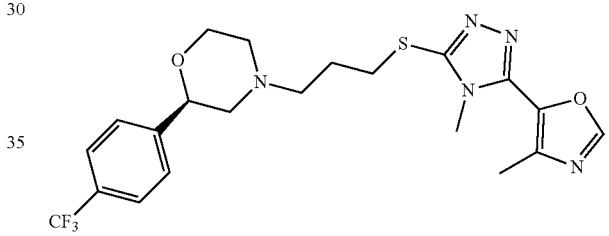

4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine (E7, 35 mg) was separated into the single enantiomers by preparative chiral HPLC, obtaining 8.5 mg of (2S or 2R)-4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine (E8, Enantiomer 1) and 10.8 mg of (2R or 2S)-4-(3-({[4-methyl-5-(4-methyl-1,3-oxazol-5-yl)-4H-1,2,4-triazol-3-yl]sulfanyl})propyl)-2-[4-(trifluoromethyl)phenyl]morpholine (E9, Enantiomer 2).

Preparative Chromatography:

| | |
|---|---|
| Column | Chiralcel OJ-H (25 × 2 cm), 5 μm |
| Mobile phase | n-Hexane/(Ethanol + 0.1% ipa) 50/50 v/v |
| Flow rate (mL/min) | 14 |
| DAD detection | 220 nm |
| Loop | 750 μL |
| injection | 17 mg (each injection) |

Example 8 Enantiomer 1: ret. time 9.6 min, 100% ee. MS (m/z): 418.3 [MH]⁺. Example 9 Enantiomer 2: ret. time 13.4 min, 100% ee. MS (m/z): 418.3 [MH]⁺.

Example 10

(2R or 2S)-4-(3-({[4-methyl-5-(4-methyl-1,3-oxazol-5-yl)-4H-1,2,4-triazol-3-yl]sulfanyl}propyl)-2-[4-(trifluoromethyl)phenyl]morpholine hydrochloride (E10, Enantiomer 2)

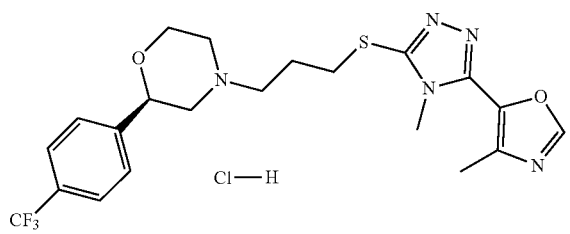 [SMILES: Cc1ncoc1-c1nnc(SCCCN2CCO[C@H](c3ccc(C(F)(F)F)cc3)C2)n1C ; Cl]

(2R or 2S)-4-(3-({[4-methyl-5-(4-methyl-1,3-oxazol-5-yl)-4H-1,2,4-triazol-3-yl]sulfanyl}propyl)-2-[4-(trifluoromethyl)phenyl]morpholine (E9, Enantiomer 2, 19.1 mg) was dissolved in Et$_2$O and treated with HCl 2 M in Et$_2$O (1.2 eq). Solvent was eliminated under reduced pressure and the residue triturated with Et$_2$O. Solvent was eliminated under reduced pressure and the residue dried under high vacuum affording (2R or 2S)-4-(3-{[4-methyl-5-(4-methyl-1,3-oxazol-5-yl)-4H-1,2,4-triazol-3-yl]sulfanyl}propyl)-2-[4-(trifluoromethyl)phenyl]-morpholine hydrochloride (E10, Enantiomer 2, 18.6 mg). NMR: $^1$H NMR (DMSO-d$_6$) δ: 10.18-10.29 (m, 1H), 8.58 (s, 1H), 7.81 (d, 2H), 7.67 (s, 2H), 4.87-4.94 (m, 1H), 4.20-4.28 (m, 1H), 3.91-3.99 (m, 1H), 3.75-3.86 (m, 2H), 3.69 (s, 3H), 3.51-3.62 (m, 2H), 3.25-3.34 (m, 3H), 3.03-3.12 (m, 2H), 2.38 (s, 2H), 2.15-2.24 (m, 2H). MS (m/z): 468.4 [MH]$^+$.

Example 11

4-{4-methyl-5-[(3-{2-[4-(trifluoromethyl)phenyl]-morpholin-4-yl}propyl)sulfanyl]-4H-1,2,4-triazol-3-yl}benzamide (E11)

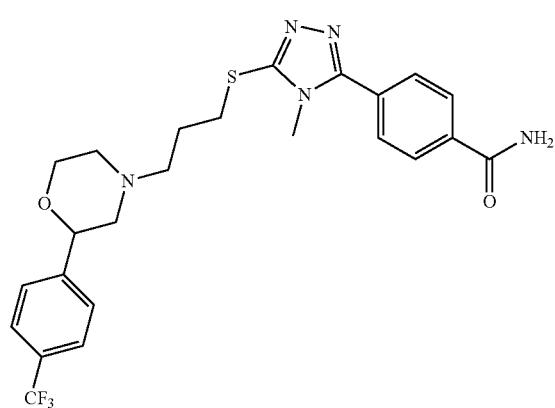

The title compound was prepared in analogy to the method described in Example 1 in 62.6 mg yield (E11, y=52%) from 2-[4-(trifluoromethyl)phenyl]morpholine (p54, 50 mg, 0.22 mmol) and 4-{5-[(3-chloropropyl)sulfanyl]-4-methyl-4H-1,2,4-triazol-3-yl}benzamide (p26, 75 mg, 0.24 mmol). NMR: $^1$H NMR (DMSO-d$_6$) δ: 8.09-8.15 (m, 1H), 8.02 (s, 2H), 7.83 (s, 2H), 7.67-7.72 (m, 2H), 7.59-7.64 (m, 2H), 7.49-7.54 (m, 1H), 4.57-4.63 (m, 1H), 3.94-4.01 (m, 1H), 3.66-3.73 (m, 1H), 3.64 (s, 3H), 3.21-3.28 (m, 2H), 2.96-3.03 (m, 1H), 2.76-2.82 (m, 1H), 2.44-2.49 (m, 2H), 2.08-2.17 (m, 1H), 1.83-1.95 (m, 3H). MS (m/z): 506.0 [MH]$^+$.

Example 12 and 13

4-[4-methyl-5-({3-[(2S or 2R)-2-[4-(trifluoromethyl)phenyl]morpholin-4-yl]propyl}sulfanyl)-4H-1,2,4-triazol-3-yl]benzamide (E12, Enantiomer 1)

4-[4-methyl-5-({3-[(2R or 2S)-2-[4-(trifluoromethyl)phenyl]morpholin-4-yl]propyl}sulfanyl)-4H-1,2,4-triazol-3-yl]benzamide (E13, Enantiomer 2)

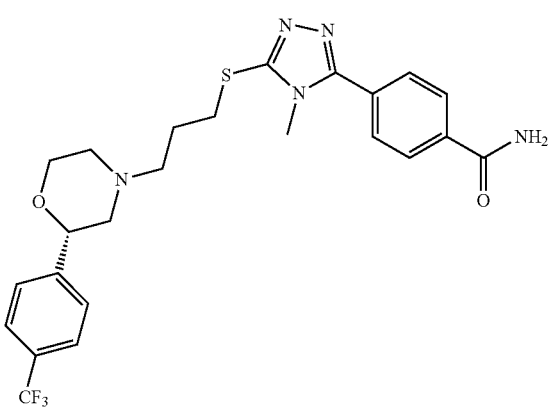 [SMILES: Cn1c(SCCCN2CCOC(c3ccc(C(F)(F)F)cc3)C2)nnc1-c1ccc(C(N)=O)cc1]

4-{4-methyl-5-[(3-{2-[4-(trifluoromethyl)phenyl]morpholine-4-yl}propyl)sulfanyl]-4H-1,2,4-triazol-3-yl}benzamide (E1, 60 mg) was separated into the single enantiomers by preparative chiral HPLC, obtaining 23.6 mg of 4-[4-methyl-5-({3-[(2S or 2R)-2-[4-(trifluoromethyl)phenyl]morpholin-4-yl]propyl}sulfanyl)-4H-1,2,4-triazol-3-yl]benzamide (E12, Enantiomer 1) and 21.9 mg of 4-[4-methyl-5-({3-[(2R or 2S)-2-[4-(trifluoromethyl)phenyl]morpholine-4-yl]propyl}sulfanyl)-4H-1,2,4-triazol-3-yl]benzamide (E13, Enantiomer 2).

Preparative Chromatography:

| Column | Chiralcel OJ-H (25 × 2.0 cm), 5μ |
|---|---|
| Mobile phase | n-Hexane/(Ethanol/Methanol 1/1 + 0.1% isopropylamine) 30/70% v/v |
| Flow rate (mL/min) | 18 |
| DAD detection | 220 nm |
| Loop | 3000 μL |
| injection | 9 mg (each injection) |

Example 12, Enantiomer 1: ret. time 7.5 min, 100% ee. MS (m/z): 506.3 [MH]⁺. Example 13, Enantiomer 2: ret. time 8.8 min, 100% ee. MS (m/z): 506.3 [MH]⁺.

Example 14

4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine (E14)

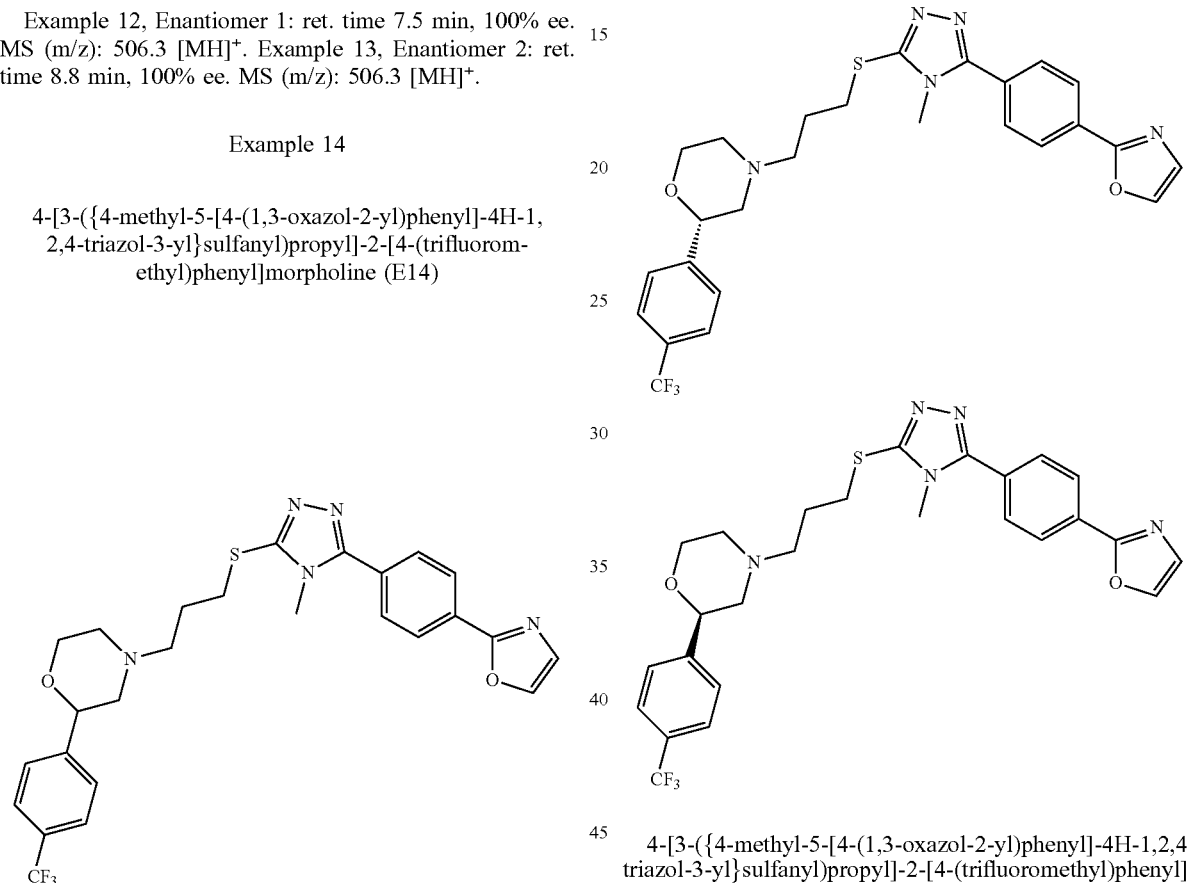

The title compound was prepared in analogy to the method described in Example 1 in 36.2 mg yield (E14, y=45%) from 2-[4-(trifluoromethyl)phenyl]morpholine (p54, 35 mg, 0.15 mmol) and 3-[(3-chloropropyl)sulfanyl]-4-methyl-5-[4-(1,3-oxazol-2-yl)phenyl]-4H-1,2,4-triazole (p27, 50 mg, 0.15 mmol). NMR: ¹H NMR (Acetone-d₆) δ: 8.20 (s, 2H), 8.10 (d, 1H), 7.95 (d, 2H), 7.69 (s, 4H), 7.36-7.39 (m, 1H), 4.62-4.68 (m, 1H), 3.99-4.06 (m, 1H), 3.79 (s, 4H), 3.37-3.46 (m, 1H), 3.27-3.36 (m, 1H), 3.13 (d, 1H), 2.82-2.88 (m, 1H), 2.56 (m, 2H), 2.16-2.25 (m, 2H), 1.99-2.03 (m, 1H), 1.88-1.95 (m, 1H). MS (m/z): 530.3 [MH]⁺.

Example 15 and 16

(2S or 2R)-4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine (E15, Enantiomer 1)

(2R or 2S)-4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine (E16, Enantiomer 2)

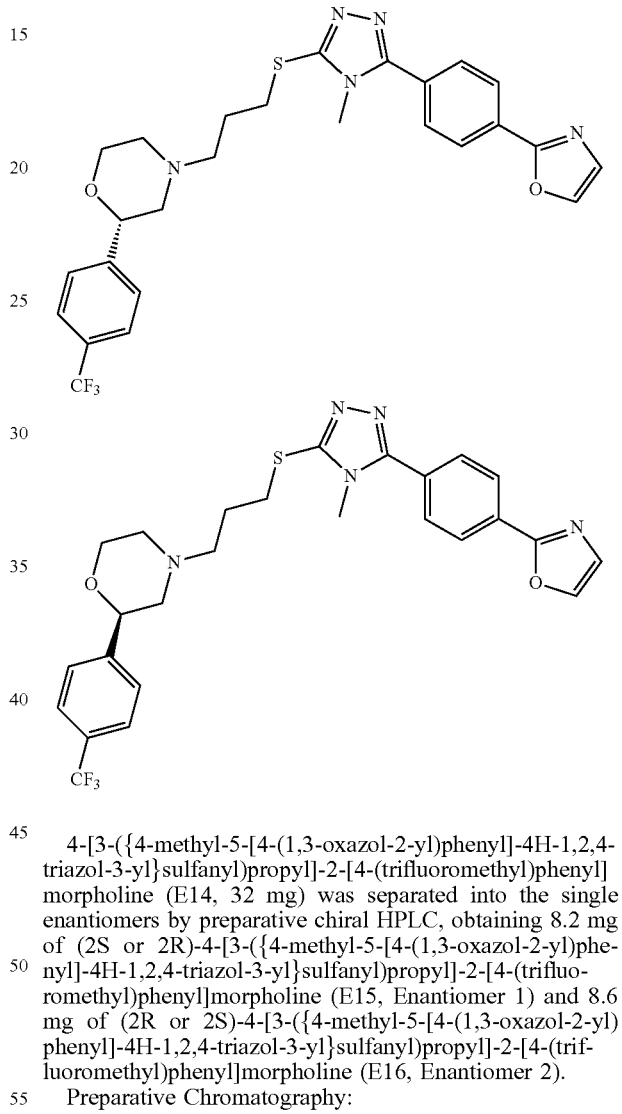

4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine (E14, 32 mg) was separated into the single enantiomers by preparative chiral HPLC, obtaining 8.2 mg of (2S or 2R)-4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine (E15, Enantiomer 1) and 8.6 mg of (2R or 2S)-4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine (E16, Enantiomer 2).

Preparative Chromatography:

| Column | Chiralcel OJ-H (25 × 2.0 cm), 5μ |
|---|---|
| Mobile phase | n-Hexane/(2-Propanol/Methanol 1/1 + 0.1% isopropylamine) 40/60% v/v |
| Flow rate (mL/min) | 18 |
| DAD detection | 220 nm |
| Loop | 1500 μL |
| injection | 16 mg (each injection) |

Example 15 Enantiomer 1: ret. time 8.1 min, 100% ee. MS (m/z): 530.3 [MH]⁺. Example 16 Enantiomer 2: ret. time 12.6 min, 100% ee. MS (m/z): 530.3 [MH]⁺.

The examples listed in Table 3 were synthesized in analogy with Example 1, reacting 2-[4-(trifluoromethyl)phenyl]morpholine (p54) with preparations p28-44.

TABLE 3

| Comp. | Intermediate | Yield % |
|---|---|---|
| 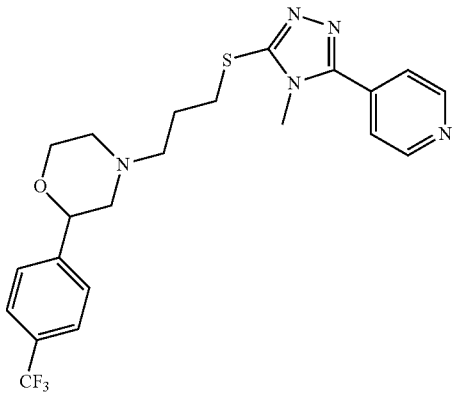<br>E17 | p28<br>¹H NMR (Acetone-d₆) δ: 8.75-8.80 (m, 2H), 7.75-7.81 (m, 2H), 7.69 (s, 4H), 4.62-4.70 (m, 1H), 3.98-4.07 (m, 1H), 3.82 (s, 3H), 3.75-3.80 (m, 1H), 3.39-3.48 (m, 1H), 3.35 (s, 1H), 3.13 (d, 1H), 2.84 (br. s., 1H), 2.55 (d, 2H), 2.17-2.25 (m, 2H), 1.97-2.04 (m, 1H), 1.92 (s, 1H)<br>MS (m/z): 464.4 [MH]⁺. | 43 |

4-(3-{[4-methyl-5-(pyridin-4-yl)-4H-1,2,4-triazol-3-yl]sulfanyl}propyl)-2-[4-(trifluoromethyl)phenyl]morpholine

| | | |
|---|---|---|
| 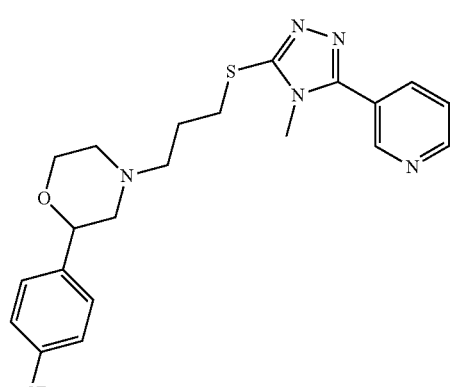<br>E18 | p29<br>¹H NMR (Acetone-d₆) δ: 8.96-9.01 (m, 1H), 8.72-8.77 (m, 1H), 8.15-8.21 (m, 1H), 7.70 (s, 4H), 7.56-7.61 (m, 1H), 4.64-4.70 (m, 1H), 4.01-4.07 (m, 1H), 3.74-3.86 (m, 4H), 3.41 (s, 1H), 3.35 (s, 1H), 3.11-3.18 (m, 1H), 2.84-2.91 (m, 1H), 2.51-2.63 (m, 2H), 2.18-2.27 (m, 2H), 2.00-2.05 (m, 1H), 1.90-1.97 (m, 1H)<br>MS (m/z): 464.4 [MH]⁺. | 21 |

4-(3-{[4-methyl-5-(pyridin-3-yl)-4H-1,2,4-triazol-3-yl]sulfanyl}propyl)-2-[4-(trifluoromethyl)phenyl]morpholine

| | | |
|---|---|---|
| 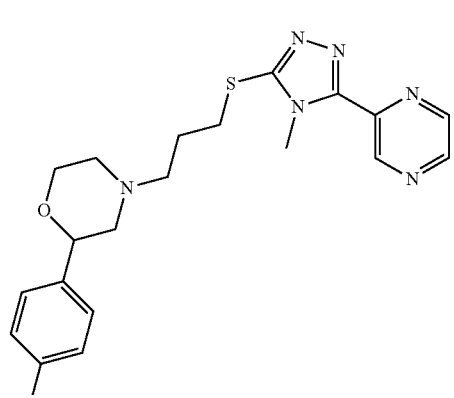<br>E19 | p30<br>¹H NMR (Acetone-d₆) δ: 9.39-9.44 (m, 1H), 8.69-8.77 (m, 2H), 7.70 (s, 4H), 4.63-4.71 (m, 1H), 4.04 (s, 4H), 3.76-3.85 (m, 1H), 3.44-3.52 (m, 1H), 3.33-3.42 (m, 1H), 3.11-3.17 (m, 1H), 2.84-2.89 (m, 1H), 2.53-2.62 (m, 2H), 2.18-2.27 (m, 2H), 2.01-2.05 (m, 1H), 1.90-1.97 (m, 1H)<br>MS (m/z): 465.4 [MH]⁺. | 39 |

4-(3-{[4-methyl-5-(pyrazin-2-yl)-4H-1,2,4-triazol-3-yl]sulfanyl}propyl)-2-[4-(trifluoromethyl)phenyl]morpholine TABLE 3-continued

| Comp. | Intermediate | Yield % |
|---|---|---|
| 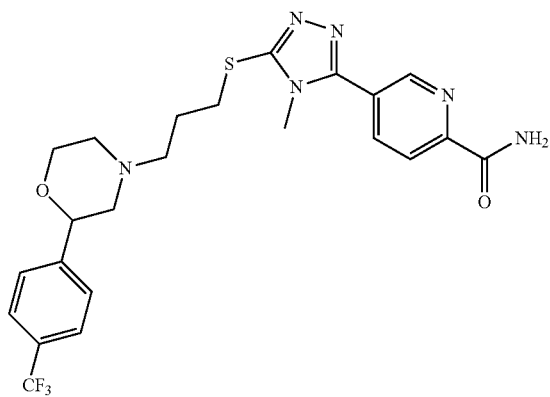<br>E20<br>5-{4-methyl-5-[(3-{2-[4-(trifluoromethyl)phenyl]morpholin-4-yl}propyl)sulfanyl]-4H-1,2,4-triazol-3-yl}pyridine-2-carboxamide | p31 | 52<br>$^1$H NMR (Acetone-d$_6$) δ: 8.99-9.03 (m, 1H), 8.37 (d, 1H), 8.30 (d, 1H), 7.98-8.06 (m, 1H), 7.70 (s, 4H), 6.88-6.98 (m, 1H), 4.63-4.70 (m, 1H), 3.99-4.06 (m, 1H), 3.82 (s, 3H), 3.80 (d, 1H), 3.40-3.48 (m, 1H), 3.30-3.39 (m, 1H), 3.11-3.17 (m, 1H), 2.84-2.89 (m, 1H), 2.52-2.62 (m, 2H), 2.17-2.26 (m, 2H), 2.00-2.04 (m, 1H), 1.89-1.96 (m, 1H)<br>MS (m/z): 507.0 [MH]$^+$. |
| 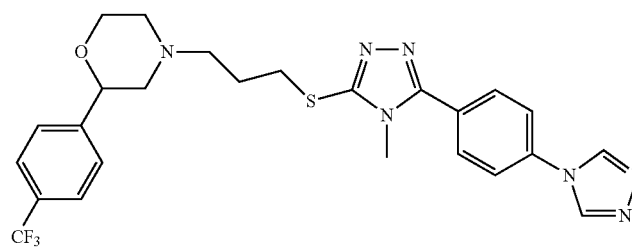<br>E21<br>4-[3-({4-methyl-5-[4-(4H-1,2,4-triazol-4-yl)phenyl]-4H-1,2,4-triazol-3-yl}sulfanyl)propyl]-2-[4-(trifluoromethyl)phenyl]morpholine | p32 | 44<br>$^1$H NMR (Acetone-d$_6$) δ: 8.97 (s, 2H), 7.98-8.03 (m, 2H), 7.89-7.94 (m, 2H), 7.70 (s, 4H), 4.63-4.69 (m, 1H), 4.00-4.06 (m, 1H), 3.79 (s, 4H), 3.38-3.48 (m, 1H), 3.30-3.36 (m, 1H), 3.12-3.18 (m, 1H), 2.83-2.89 (m, 1H), 2.51-2.62 (m, 2H), 2.17-2.27 (m, 2H), 1.99-2.04 (m, 1H), 1.89-1.96 (m, 1H)<br>MS (m/z): 530.3 [MH]$^+$. |
| 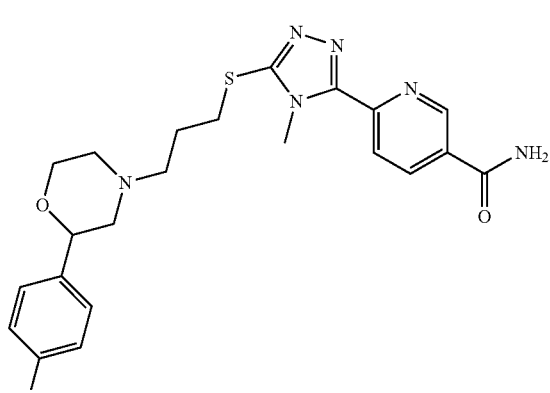<br>E22<br>6-{4-methyl-5-[(3-{2-[4-(trifluoromethyl)phenyl]morpholin-4-yl}propyl)sulfanyl]-4H-1,2,4-triazol-3-yl}pyridine-3-carboxamide | p33 | 32<br>$^1$H NMR (Acetone-d$_6$) δ: 9.18-9.22 (m, 1H), 8.41-8.46 (m, 1H), 8.31-8.36 (m, 1H), 7.67-7.72 (m, 4H), 4.61-4.68 (m, 1H), 4.08 (s, 3H), 3.99-4.05 (m, 1H), 3.75-3.83 (m, 1H), 3.44 (s, 1H), 3.31-3.39 (m, 1H), 3.13 (d, 1H), 2.83-2.89 (m, 1H), 2.52-2.59 (m, 2H), 2.17-2.25 (m, 2H), 2.00-2.04 (m, 1H), 1.88-1.92 (m, 1H)<br>MS (m/z): 507.3 [MH]$^+$. |

TABLE 3-continued

| Comp. | Intermediate | Yield % |
|---|---|---|
| 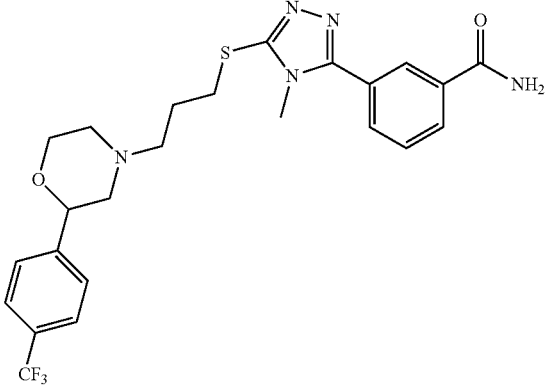 E23 | p34 | 38 |

$^1$H NMR (Acetone-$d_6$) δ: 8.28 (s, 1H), 8.08-8.13 (m, 1H), 7.90-7.95 (m, 1H), 7.69 (s, 5H), 4.63-4.69 (m, 1H), 3.99-4.06 (m, 1H), 3.79 (d, 1H), 3.76 (s, 3H), 3.36-3.45 (m, 1H), 3.27-3.36 (m, 1H), 3.09-3.16 (m, 1H), 2.83-2.89 (m, 1H), 2.53-2.59 (m, 2H), 2.22 (s, 2H), 2.00-2.04 (m, 1H), 1.89-1.96 (m, 1H)
MS (m/z): 506.3 [MH]$^+$.

3-{4-methyl-5-[(3-{2-[4-(trifluoromethyl)phenyl]morpholin-4-yl}propyl)sulfanyl]-4H-1,2,4-triazol-3-yl}benzamide

| | | |
|---|---|---|
| 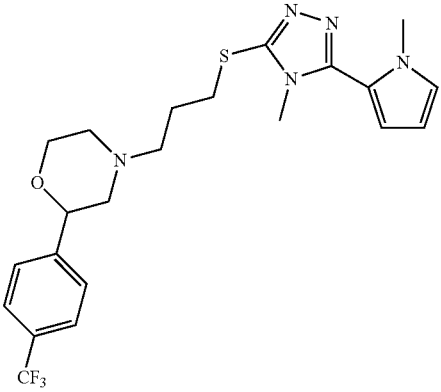 E24 | p35 | 16 |

$^1$H NMR (Acetone-$d_6$) δ: 7.69 (s, 4H), 6.92-7.02 (m, 1H), 6.48-6.58 (m, 1H), 6.18-6.28 (m, 1H), 4.62-4.72 (m, 1H), 3.99-4.07 (m, 1H), 3.88 (s, 3H), 3.75-3.85 (m, 1H), 3.69 (s, 3H), 3.36-3.46 (m, 1H), 3.23-3.33 (m, 1H), 3.12-3.18 (m, 1H), 2.83-2.87 (m, 1H), 2.49-2.62 (m, 2H), 2.16-2.28 (m, 2H), 1.97-2.05 (m, 1H), 1.88-1.95 (m, 1H)
MS (m/z): 466.4 [MH]$^+$.

4-(3-{[4-methyl-5-(1-methyl-1H-pyrrol-2-yl)-4H-1,2,4-triazol-3-yl]sulfanyl}propyl)-2-[4-(trifluoromethyl)phenyl]morpholine

| | | |
|---|---|---|
| 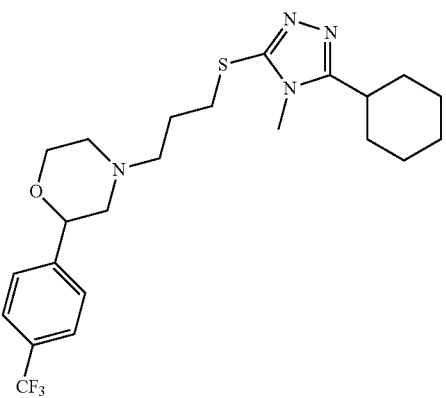 E25 | p36 | 31 |

$^1$H NMR (Acetone-$d_6$) δ: 7.71 (s, 4H), 4.60-4.76 (m, 1H), 3.96-4.09 (m, 1H), 3.72-3.89 (m, 2H), 3.59 (s, 3H), 3.31 (d, 2H), 3.08-3.25 (m, 2H), 2.44-2.64 (m, 3H), 2.18-2.28 (m, 1H), 1.90-2.02 (m, 4H), 1.82-1.90 (m, 2H), 1.71-1.80 (m, 1H), 1.58-1.70 (m, 2H), 1.30-1.52 (m, 3H)
MS (m/z): 469.4 [MH]$^+$.

4-{3-[(5-cyclohexyl-4-methyl-4H-1,2,4-triazol-3-yl)sulfanyl]propyl}-2-[4-(trifluoromethyl)phenyl]morpholine TABLE 3-continued

| Comp. | Intermediate | Yield % |
|---|---|---|
| 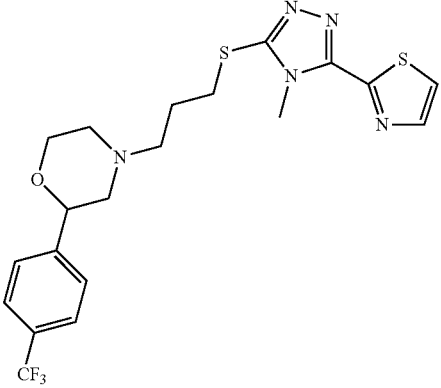<br>E26 | p37 | 60 |

¹H NMR (Acetone-d₆) δ: 8.05 (d, 1H), 7.82 (d, 1H), 7.70 (s, 4H), 4.61-4.72 (m, 1H), 4.07 (s, 3H), 4.00-4.06 (m, 1H), 3.75-3.87 (m, 1H), 3.43-3.53 (m, 1H), 3.30-3.41 (m, 1H), 3.10-3.18 (m, 1H), 2.83-2.90 (m, 1H), 2.48-2.64 (m, 2H), 2.18-2.29 (m, 2H), 2.01-2.06 (m, 1H), 1.84-1.95 (m, 1H)
MS (m/z): 470.3 [MH]⁺.

4-(3-{[4-methyl-5-(1,3-thiazol-2-yl)-4H-1,2,4-triazol-3-yl]sulfanyl}propyl)-2-[4-(trifluoromethyl)phenyl]morpholine

| | | |
|---|---|---|
| 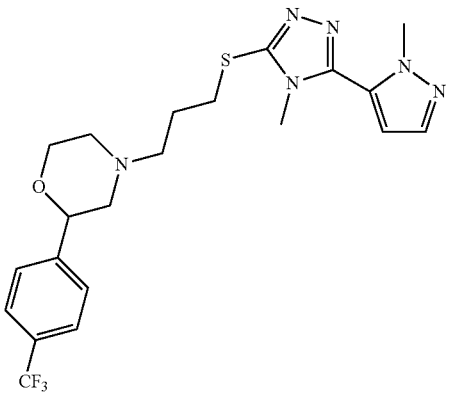<br>E27 | p38 | 36 |

¹H NMR (Acetone-d₆) δ: 7.70 (s, 4H), 7.57-7.61 (m, 1H), 6.72-6.76 (m, 1H), 4.63-4.70 (m, 1H), 4.08 (s, 3H), 4.01-4.06 (m, 1H), 3.76-3.86 (m, 1H), 3.71 (s, 3H), 3.39-3.50 (m, 1H), 3.30-3.38 (m, 1H), 3.11-3.19 (m, 1H), 2.83-2.89 (m, 1H), 2.50-2.64 (m, 3H), 2.18-2.29 (m, 2H), 1.99-2.05 (m, 1H), 1.89-1.97 (m, 1H)
MS (m/z): 467.4 [MH]⁺.

4-(3-{[4-methyl-5-(1-methyl-1H-pyrazol-5-yl)-4H-1,2,4-triazol-3-yl]sulfanyl}propyl)-2-[4-(trifluoromethyl)phenyl]morpholine

| | | |
|---|---|---|
| 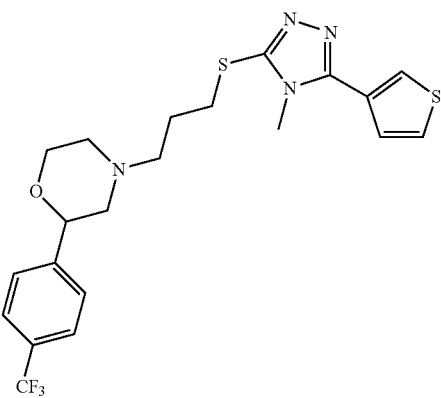<br>E28 | p39 | 41 |

¹H NMR (Acetone-d₆) δ: 8.00 (m, 1H), 7.70 (br. s., 1H), 7.69 (s, 4H), 7.61-7.65 (m, 1H), 4.61-4.68 (m, 1H), 3.99-4.07 (m, 1H), 3.82 (s, 3H), 3.75-3.80 (m, 1H), 3.34-3.43 (m, 1H), 3.23-3.33 (m, 1H), 3.08-3.15 (m, 1H), 2.82-2.88 (m, 1H), 2.55 (m, 2H), 2.17-2.26 (m, 1H), 1.97-2.04 (m, 2H), 1.92 (s, 1H)
MS (m/z): 469.4 [MH]⁺.

4-(3-{[4-methyl-5-(thiophen-3-yl)-4H-1,2,4-triazol-3-yl]sulfanyl}propyl)-2-[4-(trifluoromethyl)phenyl]morpholine

TABLE 3-continued

| Comp. | Intermediate | Yield % |
|---|---|---|
| 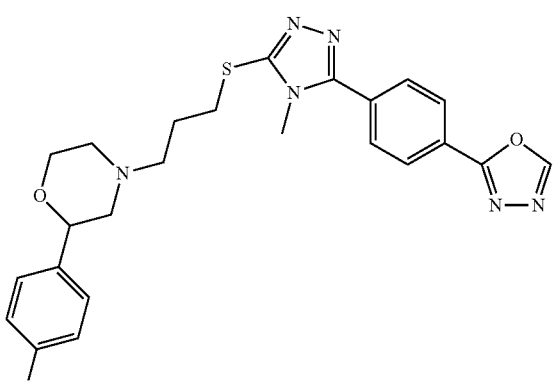<br>E29 | p40 | 3 |
| | ¹H NMR (Acetone-$d_6$) δ: 9.07 (s, 1H), 8.27 (s, 2H), 8.05 (d, 2H), 7.70 (s, 4H), 4.64-4.70 (m, 1H), 4.00-4.08 (m, 1H), 3.82 (s, 3H), 3.81 (d, 1H), 3.43 (s, 1H), 3.36 (s, 1H), 3.11-3.18 (m, 1H), 2.84-2.90 (m, 1H), 2.51-2.64 (m, 2H), 2.23 (d, 1H), 2.04 (br. s., 2H), 1.94 (s, 1H)<br>MS (m/z): 531.4 [MH]⁺. | |

4-[3-({4-methyl-5-[4-(1,3,4-oxadiazol-2-yl)phenyl]-4H-1,2,4-triazol-3-yl}sulfanyl)propyl]-2-[4-(trifluoromethyl)phenyl]morpholine

| | p41 | 27 |
|---|---|---|
| 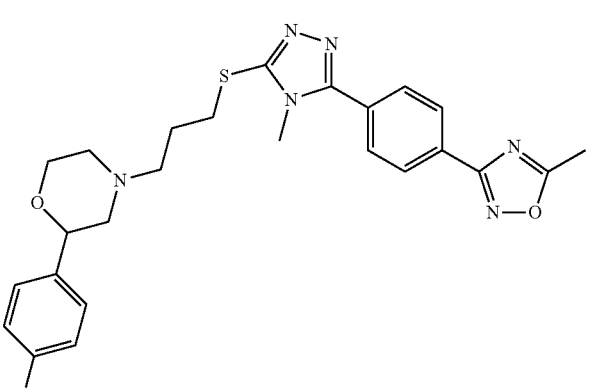<br>E30 | ¹H NMR (Acetone-$d_6$) δ: 8.22-8.27 (m, 2H), 7.95-8.01 (m, 2H), 7.70 (s, 4H), 4.67 (m, 1H), 4.02 (m, 1H), 3.74-3.86 (m, 4H), 3.39-3.49 (m, 1H), 3.28-3.38 (m, 1H), 3.10-3.18 (m, 1H), 2.84-2.91 (m, 1H), 2.72 (s, 3H), 2.51-2.63 (m, 2H), 2.18-2.27 (m, 1H), 2.00-2.06 (m, 2H), 1.90-1.97 (m, 1H)<br>MS (m/z): 545.5 [MH]⁺. | |

4-[3-({4-methyl-5-[4-(5-methyl-1,2,4-oxadiazol-3-yl)phenyl]-4H-1,2,4-triazol-3-yl}sulfanyl)propyl]-2-[4-(trifluoromethyl)phenyl]morpholine

| | p42 | 37 |
|---|---|---|
| 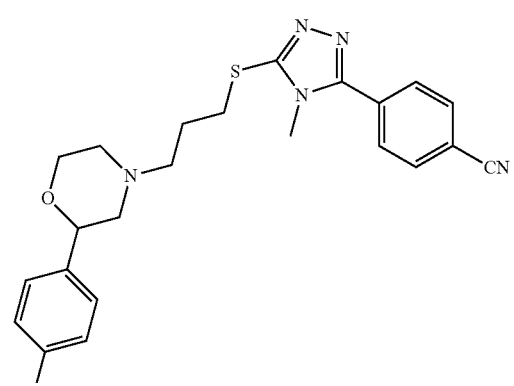<br>E31 | ¹H NMR (Acetone-$d_6$) δ: 8.02 (d, 4H), 7.70 (s, 4H), 4.63-4.70 (m, 1H), 4.02 (d, 1H), 3.77-3.86 (m, 4H), 3.40-3.48 (m, 1H), 3.30-3.38 (m, 1H), 3.12 (m, 1H), 2.84-2.89 (m, 1H), 2.57 (m, 2H), 2.23 (m, 2H), 2.00-2.04 (m, 1H), 1.90-1.96 (m, 1H)<br>MS (m/z): 488.4 [MH]⁺. | |

4-{4-methyl-5-[(3-{2-[4-(trifluoromethyl)phenyl]morpholin-4-yl}propyl)sulfanyl]-4H-1,2,4-triazol-3-yl}benzonitrile TABLE 3-continued

| Comp. | Intermediate | Yield % |
|---|---|---|
| 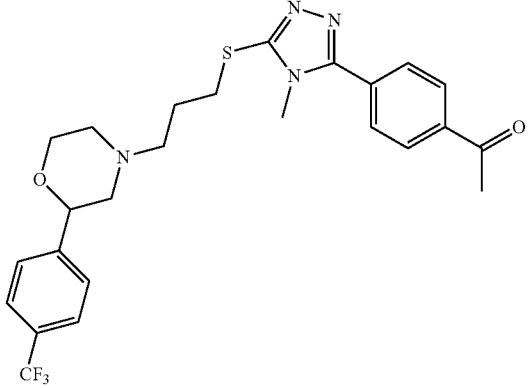 E32<br>1-(4-{4-methyl-5-[(3-{2-[4-(trifluoromethyl)phenyl]morpholin-4-yl}propyl)sulfanyl]-4H-1,2,4-triazol-3-yl}phenyl)ethan-1-one | p43<br>$^1$H NMR (Acetone-d$_6$) δ: 8.18 (d, 2H), 7.95 (d, 2H), 7.70 (s, 4H), 4.63-4.69 (m, 1H), 3.99-4.07 (m, 1H), 3.75-3.85 (m, 4H), 3.39-3.49 (m, 1H), 3.28-3.38 (m, 1H), 3.11-3.18 (m, 1H), 2.83-2.90 (m, 1H), 2.68 (s, 3H), 2.57 (d, 2H), 2.18-2.27 (m, 1H), 2.00-2.06 (m, 2H), 1.90-1.96 (m, 1H)<br>MS (m/z): 505.5 [MH]$^+$. | 41 |
| E33<br>4-{4-methyl-5-[(3-{2-[4-(trifluoromethyl)phenyl]morpholin-4-yl}propyl)sulfanyl]-4H-1,2,4-triazol-3-yl}benzene-1-sulfonamide | p44<br>$^1$H NMR (Acetone-d$_6$) δ: 8.06-8.11 (m, 2H), 7.97-8.02 (m, 2H), 7.70 (s, 4H), 6.70-6.79 (m, 1H), 4.63-4.71 (m, 1H), 4.00-4.09 (m, 1H), 3.75-3.85 (m, 4H), 3.39-3.48 (m, 1H), 3.30-3.37 (m, 1H), 3.12-3.18 (m, 1H), 2.83-2.89 (m, 1H), 2.57 (d, 2H), 2.18-2.27 (m, 1H), 2.05 (d, 2H), 1.93 (s, 1H)<br>MS (m/z): 542.4 [MH]$^+$. | 27 |

The examples listed in Table 4 were synthesized in analogy with Example 1 reacting 2-[2-fluoro-4-(trifluoromethyl)phenyl]morpholine (p59) with the defined intermediates.

TABLE 4

| Comp. | Intermediate | Yield % |
|---|---|---|
| 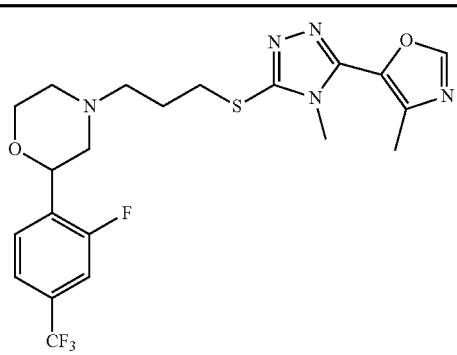 E34<br>2-[2-fluoro-4-(trifluoromethyl)phenyl]-4-(3-{[4-methyl-5-(4-methyl-1,3-oxazol-5-yl)-4H-1,2,4-triazol-3-yl]sulfanyl}propyl) | p25<br>$^1$H NMR (Acetone-d$_6$) δ: 8.28 (s, 1H), 7.76-7.82 (m, 1H), 7.57-7.63 (m, 1H), 7.48-7.54 (m, 1H), 4.84-4.92 (m, 1H), 4.00-4.08 (m, 1H), 3.80 (s, 4H), 3.28-3.39 (m, 2H), 3.02-3.09 (m, 1H), 2.85-2.91 (m, 1H), 2.54-2.60 (m, 2H), 2.43 (s, 3H), 2.19-2.28 (m, 2H), 1.99-2.04 (m, 2H)<br>MS (m/z): 486.3 [MH]$^+$. | 50 |

TABLE 4-continued

| Comp. | Intermediate | Yield % |
|---|---|---|
| morpholine 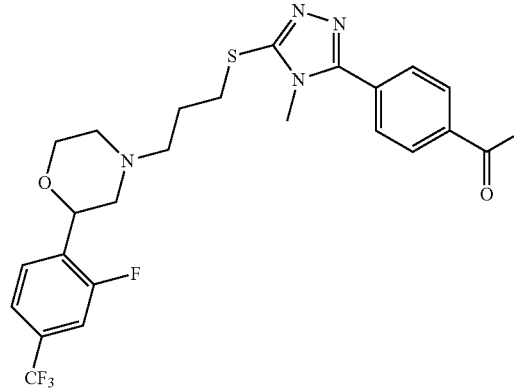 E35 | p26 ¹H NMR (Acetone-d₆) δ: 8.09-8.15 (m, 2H), 7.85-7.90 (m, 2H), 7.80 (s, 1H), 7.61 (d, 2H), 7.52 (d, 1H), 6.68-6.82 (m, 1H), 4.86-4.93 (m, 1H), 4.02-4.09 (m, 1H), 3.80-3.88 (m, 1H), 3.78 (s, 3H), 3.29-3.41 (m, 2H), 3.04-3.10 (m, 1H), 2.88-2.94 (m, 1H), 2.56-2.61 (m, 2H), 2.21-2.29 (m, 2H), 1.99-2.05 (m, 2H) MS (m/z): 524.3 [MH]⁺. | 38 |

4-{5-[(3-{2-[2-fluoro-4-(trifluoromethyl)phenyl]morpholin-4-yl}propyl)sulfanyl]-4-methyl-4H-1,2,4-triazol-3-yl}benzamide The examples listed in Table 5 were synthesized in analogy with Example 1 reacting 2-(4-methylphenyl)morpholine (commercially available from Enamine) with the defined intermediates.

TABLE 5

| Comp. | Intermediate | Yield % |
|---|---|---|
| 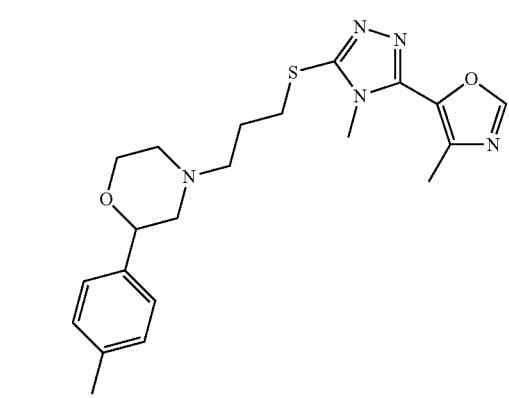 E36 | p25 ¹H NMR (Acetone-d₆) δ: 8.27 (s, 1H), 7.27 (s, 2H), 7.15 (s, 2H), 4.43-4.50 (m, 1H), 3.92-3.99 (m, 1H), 3.80 (s, 3H), 3.69-3.77 (m, 1H), 3.26-3.44 (m, 3H), 2.93-2.99 (m, 1H), 2.80 (s, 2H), 2.49-2.54 (m, 2H), 2.42-2.44 (m, 3H), 2.29-2.32 (m, 3H), 2.12-2.20 (m, 1H), 1.97-2.03 (m, 2H), 1.91-1.95 (m, 1H) MS (m/z): 414.5 [MH]⁺. | 72 |

4-(3-{[4-methyl-5-(4-methyl-1,3-oxazol-5-yl)-4H-1,2,4-triazol-3-yl]sulfanyl}propyl)-2-(4-methylphenyl)morpholine

TABLE 5-continued

| Comp. | | Intermediate | Yield % |
|---|---|---|---|
| 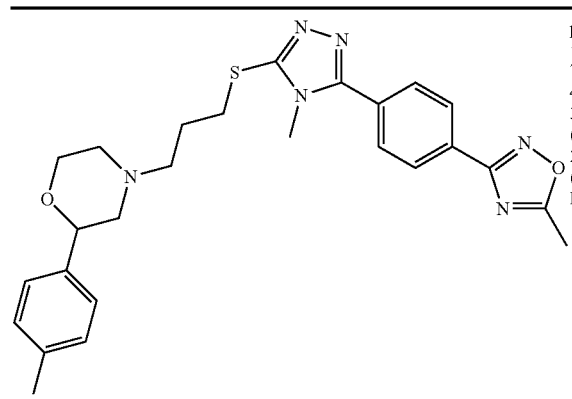 E37 | | p41 | 66 |

¹H NMR (Acetone-d₆) δ: 8.20-8.26 (m, 2H), 7.98 (s, 7H), 7.26-7.32 (m, 2H), 7.12-7.17 (m, 2H), 4.44-4.52 (m, 1H), 3.93-4.00 (m, 1H), 3.80 (s, 3H), 3.70-3.78 (m, 1H), 3.29-3.41 (m, 2H), 2.96-3.00 (m, 1H), 2.83-2.86 (m, 1H), 2.69-2.74 (m, 3H), 2.50-2.57 (m, 2H), 2.29-2.34 (m, 3H), 2.12-2.24 (m, 2H), 2.00-2.03 (m, 1H), 1.89-1.97 (m, 1H) MS (m/z): 491.4 [MH]⁺.

4-[3-({4-methyl-5-[4-(5-methyl-1,2,4-oxadiazol-3-yl)phenyl]-4H-1,2,4-triazol-3-yl}sulfanyl)propyl]-2-(4-methylphenyl)morpholine

Example 38

2-(4-bromophenyl)-4-(3-{[4-methyl-5-(4-methyl-1,3-oxazol-5-yl)-4H-1,2,4-triazol-3-yl]sulfanyl}propyl)morpholine (E38)

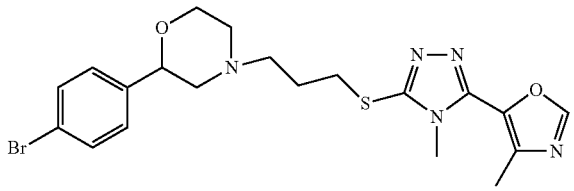 [SMILES: Cc1ncoc1-c1nnc(SCCCN2CCOC(c3ccc(Br)cc3)C2)n1C]

The title compound was prepared in analogy to the method described in Example 1 in 40 mg yield (E14, y=56%) from 2-(4-bromophenyl)morpholine (commercially available from Enamine, 36 mg, 0.15 mmol) and 3-[(3-chloropropyl)sulfanyl]-4-methyl-5-(4-methyl-1,3-oxazol-5-yl)-4H-1,2,4-triazole (p25, 41 mg, 0.15 mmol). NMR: ¹H NMR (Acetone-d₆) δ: 8.28 (s, 1H), 7.52 (d, 2H), 7.40 (d, 2H), 4.49-4.55 (m, 1H), 3.96-4.01 (m, 1H), 3.80 (s, 3H), 3.72-3.78 (m, 1H), 3.36-3.44 (m, 1H), 3.26-3.34 (m, 1H), 3.03-3.08 (m, 1H), 2.53 (m, 2H), 2.44 (s, 3H), 2.14-2.19 (m, 1H), 1.97-2.04 (m, 2H), 1.85-1.92 (m, 1H) MS (m/z): 478.3 [MH]⁺.

Example 39

Biological Test Methods

[³H]-Spiperone Binding Assay at hD₃ and hD₄ recombinant receptors CHO cells transiently transfected with human dopamine type 3 or 4 receptors (CHO-hD₃ or CHO-hD₄, respectively), were re-suspended in 20 mM HEPES, 2 mM EDTA (pH 7.4), homogenised and centrifuged at 40,000 g (20 min, 4° C.). After re-suspension, homogenization and centrifugation as above, the final pellet was re-suspended in 20 mM HEPES, 100 mM NaCl, 10 mM MgCl₂, 1 mM EDTA (pH 7.4) and aliquots were kept at −80° C. [³H]-Spiperone Binding experiments were performed in 96 deep-well polypropylene plates in 50 mM Tris/HCl, 120 mM NaCl, 5 mM KCl, 5 mM MgCl₂ (pH 7.4). Compounds of invention were serially diluted in DMSO at 100 fold final concentrations in the assay (1% DMSO final in the assay). Displacement was performed in the presence of 0.3 nM [³H]-Spiperone. The reaction was initiated by the addition of membrane suspension (4 μg and 12 μg of protein for CHO-hD₃- and CHO-hD₄ membranes, respectively) and lasted for 90 or 100 min (for hD₃ or hD₄ membranes, respectively) at 23° C. in a final volume of 500 μl. Non specific binding (NSB) was determined in the presence of 1 μM Spiperone. The binding reaction was stopped by rapid filtration through GF/B filterplates pre-soaked in 0.5% polyetylenimmine (PEI) using a Packard cell harvester. After washing with ice-cold 0.9% NaCl, the plate was left to dry before the addition of Microscint 20 (50 l/well, PerkinElmer). Radioactivity was counted with a TopCount (PerkinElmer). Data were analysed by non-linear regression analysis using GraphPad Prism 5.0 (GraphPad Software). Saturation binding experiments were performed similar to the competition binding experiments using a radioligand concentrations ranging from 0.015 to 4.0 nM. Ref: Mackenzie R. G. et al. (1994). Characterization of the human dopamine D3 receptor expressed in transfected cell lines. Eur. J. Pharmacol., 266:79-8

[¹²⁵I]-70H-PIPAT Binding Assay at rat native D₃ receptor on membranes from rat ventral striatum Homogenates from frozen rat brain ventral striatum (nucleus accumbens and olfactory tubercles), were prepared as described by Burris et al. (1994). [¹²⁵I]-70H-PIPAT binding assay at D₃ receptors was performed in 50 mM Tris-HCl (pH 7.0), 50 mM NaCl, 100 μM Gpp(NH)p (Guanosine 5'-[β,γ-imido]triphosphate) and 0.02% BSA, i.e. conditions which inhibit the [¹²⁵I]-7-OH-PIPAT binding to D₂ and 5HT₁ₐ receptors. Compounds of invention were serially diluted in DMSO at 100 fold final concentrations in the assay (1% DMSO final in the assay). Displacement experiments were performed in the presence of 0.2 nM [¹²⁵I]-70H-PIPAT. The reaction, carried out in a final volume of 2001 μl, was initiated by the addition of membrane suspension (about 20 μg/well protein) and lasted 45 min at 37° C. Non specific binding (NSB) was determined in the presence of 1 μM SB277011A. The binding reaction was stopped by rapid filtration through GF/C filterplates pre-soaked in 0.5% polyetylenimmine (PEI) using a Packard cell harvester. After washing with ice-cold 50 mM Tris (pH 7.4) and addition of Microscint 20 (50 l/well, PerkinElmer), radioactivity was counted with a TopcCount (PerkinElmer). Data were analyzed by non-linear regression analysis using GraphPad Prism 5.0 (GraphPad Software). Ref: Burris, K. D.; Filtz, T. M.; Chumpradit, S.; Kung, M. P.; Foulon, C.; Hensler, J. G.; Kung, H. F.; Molinoff, P. B. Characterization of [125I](R)-trans-7-hydroxy-2-[N-propyl-N-(3'-iodo-2'-propenyl)amino]tetralin binding to dopamine D3 receptors in rat olfactory tubercle. J. Pharmacol. Exp. Ther. 1994, 268, 935-942.

[$^3$H]-Spiperone Binding Assay at $hD_2$ Recombinant Receptor

CHO cells stably expressing human dopamine receptor type 2, long variant ($hD_{2L}$), coupled to Gα16 protein (CHO-Gα16-$hD_{2L}$) were re-suspended in 20 mM HEPES, 2 mM EDTA (pH 7.4), homogenised and centrifuged at 40,000 g (20 min, 4° C.). After re-suspension, homogenization and centrifugation as above, the final pellet was re-suspended in 20 mM HEPES, 100 mM NaCl, 10 mM $MgCl_2$, 1 mM EDTA (pH 7.4) and aliquots were kept at −80° C. [$^3$H]-Spiperone Binding experiments were performed in 96 deep-well polypropylene plates in 50 mM Tris/HCl, 120 mM NaCl, 5 mM KCl, 5 mM $MgCl_2$ (pH 7.4). Compounds of invention were serially diluted in DMSO at 100 fold final concentrations in the assay (1% DMSO final in the assay). Displacement was performed in the presence of 0.08 nM [$^3$H]-Spiperone. The reaction was initiated by the addition of membrane suspension (2 μg of protein for CHO-$hD_2$ membranes) and lasted for 120 min at 23° C. in a final volume of 1000 μl. Non specific binding (NSB) was determined in the presence of 0.1 μM Spiperone. The binding reaction was stopped by rapid filtration through GF/B filterplates pre-soaked in 0.5% polyetylenimmine (PEI) using a Packard cell harvester. After washing with ice-cold 0.9% NaCl, the plate was left to dry before the addition of Microscint 20 (50 μl/well, PerkinElmer). Radioactivity was counted with a TopCount (PerkinElmer). Data were analysed by non-linear regression analysis using GraphPad Prism 5.0 (GraphPad Software) or XLfit Version 5.2.0.0 (Copyright © 2006-2009 ID Business Solutions Ltd). Saturation binding experiments were performed similar to the competition binding experiments using a radioligand concentrations ranging from 0.011 to 3.0 nM. Ref: Durcan M. J. et al. (1995). Is Clozapine selective for the dopamine D4 receptor? Life Sciences, 57: 275-283. Petrus J. et al. (2001). Real-time analysis of dopamine: antagonist interactions at recombinant human D2long receptor upon modulation of its activation state. Brit. J. Pharmacol. 134, 88±97.

Functional Calcium Assay at $hD_2$ Recombinant Receptor

CHO cells stably expressing human dopamine receptor type 2, long variant ($hD_{2L}$), coupled to Gα16 protein (CHO-Gα16-$hD_{2L}$) were seeded into black walled clear-base 384-well plates at a density of 8,000 cells per well and grown overnight at 37° C. After washing with the assay buffer (20 mM HEPES, 145 mM NaCl, 5 mM KCl, 5.5 mM glucose, 1 mM $MgCl2$ and 2 mM $CaCl2$, pH 7.4) containing 2.5 mM Probenecid, cells were incubated with the cytoplasmic $Ca^{2+}$ probe Fluo-4 AM at 1 μM (final concentration), 37° C. for 60 min. Plates were washed three times as above and placed into a Fluorometric Imaging Plate Reader (FLIPR Tetra, Molecular Devices) to monitor cell fluorescence (ex=470-495 nm, em=515-575 nm) before and after the addition of different concentrations of test compounds. Compounds of invention were dissolved in DMSO and 200-fold diluted with assay buffer plus 0.01% Pluronic F-127. Cells were exposed first to test compounds for 10 min, then to a submaximal concentration of the $hD_2$ receptor agonist dopamine ($EC_{80}$, 50-140 nM). The fluorescence before compound addition (baseline) and before and after addition of agonist challenge was monitored. The peak of $Ca^{2+}$ stimulation (baseline subtracted) was plotted versus the concentration of test compound and the curve fitted using a four-parameter logistic equation (XLfit) to assess the agonist/antagonist potency and maximal response.

The compounds of the invention listed above have pKi values within the range of 6.0-8.5 at the dopamine D3 receptor. pKi results are only estimated to be accurate to about ±0.3-0.5.

The compounds of the invention listed above have selectivity over D2 greater than 10 fold.

The following Table 6 reports the values of some of the Examples:

TABLE 6

| EX | $D_3$ p Ki | $D_2$ fp Ki | $D_2$ p Ki |
|---|---|---|---|
| 1 | 6.37 | <5 | |
| 3 | 6.56 | <5 | |
| 4 | 7.05 | <5 | |
| 6 | 7.11 | <5 | |
| 7 | 6.9 | nt | nt |
| 9 | 7.76 | 5.64 | 5.36 |
| 10 | 7.27 | <5 | 4.93 |
| 11 | 7.46 | | 4.96 |
| 13 | 7.94 | | 4.86 |
| 14 | 8.31 | | 5.83 |
| 15 | 6.36 | | 4.81 |
| 16 | 8.23 | | 5.28 |
| 17 | 6.98 | | 4.93 |
| 18 | 6.77 | | 4.83 |
| 19 | 6.76 | | 4.99 |
| 20 | 7.45 | | 4.61 |
| 21 | 6.9 | | 5.04 |
| 22 | 7 | | 4.79 |
| 23 | 6.53 | | 4.82 |
| 24 | 6.9 | | 5.18 |
| 25 | 7.36 | | 5.05 |
| 26 | 6.55 | | 5.14 |
| 27 | 6.16 | | <5 |
| 28 | 6.95 | | 5.06 |
| 29 | 7.79 | | 4.91 |
| 30 | 7.63 | | <5 |
| 31 | 6.97 | | 4.95 |
| 32 | 7.18 | | 4.65 |
| 33 | 6.87 | | <4.5 |
| 34 | 6.71 | | 4.96 |
| 35 | 7.06 | | 4.84 |
| 36 | 6.17 | nt | nt |
| 37 | 7.07 | 4.50 | 4.50 |
| 38 | 6.72 | | 4.82 |

All publications, including but not limited to patents and patent applications, cited in this specification are herein incorporated by reference herein as though fully set forth. The present invention covers all combinations of particular groups described herein above.

What is claimed is:

1. A compound of formula (I) or a pharmaceutically acceptable salt thereof:

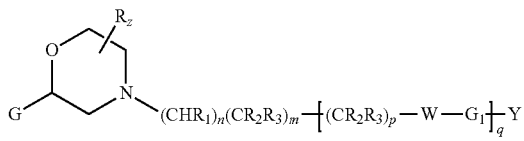

(I)

wherein:
G is aryl, a 5-6 membered heteroaromatic group, or an 8-11 membered heteroaromatic group; wherein each is optionally benzofused or optionally substituted by 1, 2, 3, or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, and $C(=O)OR_4$;

W is S, $SO_2$, O, or $NR_4$;
n is 0 or 1;
m is 1 or 2;
p is 1 or 2;
q is 1;
z in the substituent Rz is an integer ranging from 1 to 7;
R in the substituent Rz is independently hydrogen or $C_{1-4}$alkyl;
$R_1$ is hydrogen, $C_{1-4}$alkyl, or $C_{1-4}$alkoxy;
$R_2$ is hydrogen, F, $C_{1-4}$alkyl, —OH, or $C_{1-4}$alkoxy;
$R_3$ is hydrogen, F, $C_{1-4}$alkyl, or $C_{1-4}$alkoxy;
$R_4$ is hydrogen or $C_{1-4}$alkyl;
$G_1$ is a phenyl group, a 5-6-membered heteroaromatic group, or a 8-11 membered heteroaromatic group; wherein each group is optionally substituted by 1, 2, 3, or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, and $C(=O)OR_4$;
Y is phenyl, a 5-6 membered heteroaromatic group, a saturated mono 3-7 membered carbocyclic group, or 8-11 membered bicyclic carbocyclic group in which one or more atom carbons may be replaced by $NR_4$, O, S; any of which groups are optionally substituted by one or two substituents selected from the group consisting of Y', halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $SO_2NH_2$, and $C(=O)O_xR_4$;
x is 0 or 1; and
Y' is phenyl or a 5-6-membered heteroaromatic group optionally substituted by 1 or 2 $R_2$ groups;
with the proviso that $G_1$, Y, and Y' are not simultaneously phenyl.

2. The compound of claim 1, wherein the compound of formula (I) is a compound of formula (IA):

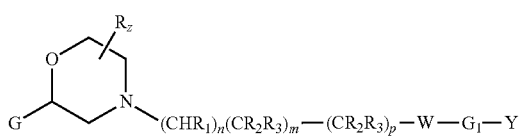

(IA)

wherein:
G is aryl or a 5-6 membered heteroaromatic group; either of which is optionally substituted by 1, 2, 3, or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, and $C(=O)OR_4$;

W is S, $SO_2$, O, or $NR_4$;
n is 0 or 1;
m is 1 or 2;
p is 1 or 2;
z in the substituent Rz is an integer from 1 to 7;
R in the substituent Rz is independently hydrogen or $C_{1-4}$alkyl;
$R_1$ is hydrogen, $C_{1-4}$alkyl, or $C_{1-4}$alkoxy;
$R_2$ is hydrogen, F, $C_{1-4}$alkyl, OH, or $C_{1-4}$alkoxy;
$R_3$ is hydrogen, F, $C_{1-4}$alkyl, or $C_{1-4}$alkoxy;
$R_4$ is hydrogen or $C_{1-4}$alkyl;
$G_1$ is a phenyl group or a 5-6-membered heteroaromatic group, either of which is optionally substituted by 1, 2, 3, or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, and $C(=O)OR_4$;
Y is a phenyl, a 5-6 membered heteroaromatic group, or an saturated mono 3-7 membered carbocyclic group; any of which groups may be optionally substituted by one or two substituents selected from the group consisting of Y', halogen, cyano, hydroxyl, amino, $C_{1}$-4alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, $SO_2NH_2$, $C(=O)O_xR_4$;
x is 0 or 1; and
Y' is phenyl or a 5-6-membered heteroaromatic group optionally substituted by 1 or 2 $R_2$ groups;
with the proviso that $G_1$, Y and Y' are not simultaneously phenyl.

3. The compound of claim 2, wherein
G is aryl which is optionally substituted by 1 or 2 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, $SF_5$, $C(=O)NH_2$, and $C(=O)OR_4$;
W is S;
n is 1;
m is 1;
p is 1;
z in the substituent Rz is an integer from 1 to 7;
R in the substituent Rz is hydrogen;
$R_2$ and $R_3$ are each hydrogen;
$R_4$ is hydrogen or $C_{1-4}$alkyl;
$G_1$ is a 5-membered heteroaromatic group containing 3 nitrogen atoms, which is optionally substituted by 1, 2, 3, or 4 substituents selected from the group consisting of halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, and $C(=O)OR_4$;
Y is a phenyl or a 5- or 6-membered heteroaromatic group, either of which is optionally substituted by Y'; and
Y' is phenyl or a 5-6-membered heteroaromatic group which is optionally substituted by 1 or 2 $R_2$ groups;
with the proviso that Y and Y' are not simultaneously phenyl.

4. A pharmaceutical composition comprising the compound of claim 1 and a pharmaceutically acceptable carrier.

5. A method for treating a dopamine $D_3$ receptor disease in a patient having said disease, the method comprising administering to the patient a therapeutically effective amount of the compound of claim 1.

6. The method of claim 5, wherein the dopamine D$_3$ receptor disease is a dyskinetic disorder, depression, anxiety, a cognitive impairment, an eating disorder, a sexual dysfunction, premature ejaculation, a sleep disorder, emesis, a movement disorder, obsessive-compulsive disorder, amnesia, aggression, autism, vertigo, dementia, a circadian rhythm disorder, or a gastric motility disorder.

7. A method of treating a psychosis or a psychotic condition in a patient having said psychosis or psychotic condition, the method comprising administering to the patient a therapeutically effective amount of the compound of claim 1.

8. A method of treating schizophrenia in a patient having schizophrenia, the method comprising administering to the patient a therapeutically effective amount of the compound of claim 1.

9. A method of treating a substance-related disorder or an addictive disorder in a patient having said disorder, the method comprising administering to the patient a therapeutically effective amount of the compound of claim 1.

10. A method of treating opioid use disorder in a patient having said disorder, the method comprising administering to the patient a therapeutically effective amount of the compound of claim 1.

11. A compound of the formula:
2-(4-fluorophenyl)-4-(3-{[4-methyl-5-(4-methyl-1,3-oxazol-5-yl)-4H-1,2,4-triazol-3-yl]sulfanyl}propyl)morpholine or a pharmaceutically acceptable salt thereof;
(2S)-2-(4-fluorophenyl)-4-(3-{[4-methyl-5-(4-methyl-1,3-oxazol-5-yl)-4H-1,2,4-triazol-3-yl]sulfanyl}propyl)morpholine or a pharmaceutically acceptable salt thereof;
(2R)-2-(4-fluorophenyl)-4-(3-{[4-methyl-5-(4-methyl-1,3-oxazol-5-yl)-4H-1,2,4-triazol-3-yl]sulfanyl}propyl)morpholine or a pharmaceutically acceptable salt thereof;
4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine or a pharmaceutically acceptable salt thereof;
(2S)-4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine or a pharmaceutically acceptable salt thereof;
(2R)-4-(4-{[4-methyl-5-(4-methyl-1,3-oxazol-5-yl)-4H-1,2,4-triazol-3-yl]sulfanyl}butyl)-2-[4-(trifluoromethyl)phenyl]morpholine or a pharmaceutically acceptable salt thereof;
4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine or a pharmaceutically acceptable salt thereof;
(2S)-4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine or a pharmaceutically acceptable salt thereof;
(2R)-4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine or a pharmaceutically acceptable salt thereof;
(2R)-4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine hydrochloride;
(2S)-4-(3-{[4-methyl-5-(4-methyl-1,3-oxazol-5-yl)-4H-1,2,4-triazol-3-yl]sulfanyl}propyl)-2-[4-(trifluoromethyl)phenyl]morpholine hydrochloride;
4-{4-methyl-5-[(3-{2-[4-(trifluoromethyl)phenyl]morpholine-4-yl}propyl)sulfanyl]-4H-1,2,4-triazol-3-yl}benzamide or a pharmaceutically acceptable salt thereof;
4-[4-methyl-5-({3-[(2S)-2-[4-(trifluoromethyl)phenyl]morpholine-4-yl]propyl}sulfanyl)-4H-1,2,4-triazol-3-yl]benzamide or a pharmaceutically acceptable salt thereof;
4-[4-methyl-5-({3-[(2R)-2-[4-(trifluoromethyl)phenyl]morpholine-4-yl]propyl}sulfanyl)-4H-1,2,4-triazol-3-yl]benzamide or a pharmaceutically acceptable salt thereof;
4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine or a pharmaceutically acceptable salt thereof;
(2S)-4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine or a pharmaceutically acceptable salt thereof;
(2R)-4-[3-({4-methyl-5-[4-(1,3-oxazol-2-yl)phenyl]-4H-1,2,4-triazol-3-yl}sulfanyl)propyl]-2-[4-(trifluoromethyl)phenyl]morpholine or a pharmaceutically acceptable salt thereof;
4-(3-{[4-methyl-5-(pyridin-4-yl)-4H-1,2,4-triazol-3-yl]sulfanyl}propyl)-2-[4-(trifluoromethyl)phenyl]morpholine or a pharmaceutically acceptable salt thereof;
4-(3-{[4-methyl-5-(pyridin-3-yl)-4H-1,2,4-triazol-3-yl]sulfanyl}propyl)-2-[4-(trifluoromethyl)phenyl]morpholine or a pharmaceutically acceptable salt thereof;
4-(3-{[4-methyl-5-(pyrazin-2-yl)-4H-1,2,4-triazol-3-yl]sulfanyl}propyl)-2-[4-(trifluoromethyl)phenyl]morpholine or a pharmaceutically acceptable salt thereof;
5-{4-methyl-5-[(3-{2-[4-(trifluoromethyl)phenyl]morpholine-4-yl}propyl)sulfanyl]-4H-1,2,4-triazol-3-yl}pyridine-2-carboxamide or a pharmaceutically acceptable salt thereof;
4-[3-({4-methyl-5-[4-(4H-1,2,4-triazol-4-yl)phenyl]-4H-1,2,4-triazol-3-yl}sulfanyl)propyl]-2-[4-(trifluoromethyl)phenyl]morpholine or a pharmaceutically acceptable salt thereof;
6-{4-methyl-5-[(3-{2-[4-(trifluoromethyl)phenyl]morpholin-4-yl}propyl)sulfanyl]-4H-1,2,4-triazol-3-yl}pyridine-3-carboxamide or a pharmaceutically acceptable salt thereof;
3-{4-methyl-5-[(3-{2-[4-(trifluoromethyl)phenyl]morpholin-4-yl}propyl)sulfanyl]-4H-1,2,4-triazol-3-yl}benzamide or a pharmaceutically acceptable salt thereof;
4-(3-{[4-methyl-5-(1-methyl-1H-pyrrol-2-yl)-4H-1,2,4-triazol-3-yl]sulfanyl}propyl)-2-[4-(trifluoromethyl)phenyl]morpholine or a pharmaceutically acceptable salt thereof;
4-{3-[(5-cyclohexyl-4-methyl-4H-1,2,4-triazol-3-yl)sulfanyl]propyl}-2-[4-(trifluoromethyl)phenyl]morpholine or a pharmaceutically acceptable salt thereof;
4-(3-{[4-methyl-5-(1,3-thiazol-2-yl)-4H-1,2,4-triazol-3-yl]sulfanyl}propyl)-2-[4-(trifluoromethyl)phenyl]morpholine or a pharmaceutically acceptable salt thereof;
4-(3-{[4-methyl-5-(1-methyl-1H-pyrazol-5-yl)-4H-1,2,4-triazol-3-yl]sulfanyl}propyl)-2-[4-(trifluoromethyl)phenyl]morpholine or a pharmaceutically acceptable salt thereof;
4-(3-{[4-methyl-5-(thiophen-3-yl)-4H-1,2,4-triazol-3-yl]sulfanyl}propyl)-2-[4-(trifluoromethyl)phenyl]morpholine or a pharmaceutically acceptable salt thereof;

4-[3-({4-methyl-5-[4-(1,3,4-oxadiazol-2-yl)phenyl]-4H-1,2,4-triazol-3-yl}sulfanyl)propyl]-2-[4-(trifluoromethyl)phenyl]morpholine or a pharmaceutically acceptable salt thereof;

4-[3-({4-methyl-5-[4-(5-methyl-1,2,4-oxadiazol-3-yl)phenyl]-4H-1,2,4-triazol-3-yl}sulfanyl)propyl]-2-[4-(trifluoromethyl)phenyl]morpholine or a pharmaceutically acceptable salt thereof;

4-{4-methyl-5-[(3-{2-[4-(trifluoromethyl)phenyl]morpholin-4-yl}propyl)sulfanyl]-4H-1,2,4-triazol-3-yl}benzonitrile or a pharmaceutically acceptable salt thereof;

1-(4-{4-methyl-5-[(3-{2-[4-(trifluoromethyl)phenyl]morpholine-4-yl}propyl)sulfanyl]-4H-1,2,4-triazol-3-yl}phenyl)ethan-1-one or a pharmaceutically acceptable salt thereof;

4-{4-methyl-5-[(3-{2-[4-(trifluoromethyl)phenyl]morpholine-4-yl}propyl)sulfanyl]-4H-1,2,4-triazol-3-yl}benzene-1-sulfonamide or a pharmaceutically acceptable salt thereof;

2-[2-fluoro-4-(trifluoromethyl)phenyl]-4-(3-{[4-methyl-5-(4-methyl-1,3-oxazol-5-yl)-4H-1,2,4-triazol-3-yl]sulfanyl}propyl)morpholine or a pharmaceutically acceptable salt thereof;

4-{5-[(3-{2-[2-fluoro-4-(trifluoromethyl)phenyl]morpholin-4-yl}propyl)sulfanyl]-4-methyl-4H-1,2,4-triazol-3-yl}benzamide or a pharmaceutically acceptable salt thereof, 4-(3-{[4-methyl-5-(4-methyl-1,3-oxazol-5-yl)-4H-1,2,4-triazol-3-yl]sulfanyl}propyl)-2-(4-methylphenyl)morpholine or a pharmaceutically acceptable salt thereof;

4-[3-({4-methyl-5-[4-(5-methyl-1,2,4-oxadiazol-3-yl)phenyl]-4H-1,2,4-triazol-3-yl}sulfanyl)propyl]-2-(4-methylphenyl)morpholine or a pharmaceutically acceptable salt thereof, or 2-(4-bromophenyl)-4-(3-{[4-methyl-5-(4-methyl-1,3-oxazol-5-yl)-4H-1,2,4-triazol-3-yl]sulfanyl}propyl)morpholine or a pharmaceutically acceptable salt thereof.

12. A pharmaceutical composition comprising the compound of claim 11 and a pharmaceutically acceptable carrier.

13. A method for treating a dopamine $D_3$ receptor disease in a patient having said disease, the method comprising administering to the patient a therapeutically effective amount of the compound of claim 11.

14. The method of claim 13, wherein the dopamine $D_3$ receptor disease is a dyskinetic disorder, depression, anxiety, a cognitive impairment, an eating disorder, a sexual dysfunction, premature ejaculation, a sleep disorder, emesis, a movement disorder, obsessive-compulsive disorder, amnesia, aggression, autism, vertigo, dementia, a circadian rhythm disorder, or a gastric motility disorder.

15. A method of treating a psychosis or a psychotic condition in a patient having said psychosis or psychotic condition, the method comprising administering to the patient a therapeutically effective amount of the compound of claim 11.

16. A method of treating schizophrenia in a patient having schizophrenia, the method comprising administering to the patient a therapeutically effective amount of the compound of claim 11.

17. A method of treating a substance-related disorder or an addictive disorder in a patient having said disorder, the method comprising administering to the patient a therapeutically effective amount of the compound of claim 11.

18. A method of treating opioid use disorder in a patient having said disorder, the method comprising administering to the patient a therapeutically effective amount of the compound of claim 11.

* * * * *